US012606865B2

(12) United States Patent
Fisher et al.

(10) Patent No.: US 12,606,865 B2
(45) Date of Patent: Apr. 21, 2026

(54) SYSTEM AND METHODS OF USING MICROFLUIDIC AGITATION TO ENHANCE MULTIPLEXED SOLID-PHASE ISOTHERMAL NUCLEIC ACID AMPLIFICATION

(71) Applicant: Redbud Labs, Inc., Research Triangle Park, NC (US)

(72) Inventors: Jay Kenneth Fisher, Research Triangle Park, NC (US); Katelyn Rose Kremer, Research Triangle Park, NC (US); Adam Dengler, Research Triangle Park, NC (US)

(73) Assignee: Redbud Labs, Inc., Research Triangle Park, NC (US)

( * ) Notice: Subject to any disclaimer, the term of this patent is extended or adjusted under 35 U.S.C. 154(b) by 543 days.

(21) Appl. No.: 18/033,843

(22) PCT Filed: Oct. 27, 2021

(86) PCT No.: PCT/US2021/056836
§ 371 (c)(1),
(2) Date: Apr. 26, 2023

(87) PCT Pub. No.: WO2022/093949
PCT Pub. Date: May 5, 2022

(65) Prior Publication Data
US 2023/0399686 A1      Dec. 14, 2023

Related U.S. Application Data

(60) Provisional application No. 63/106,490, filed on Oct. 28, 2020.

(51) Int. Cl.
C12Q 1/6853        (2018.01)
B01L 3/00          (2006.01)
B01L 7/00          (2006.01)

(52) U.S. Cl.
CPC ...... *C12Q 1/6853* (2013.01); *B01L 3/502707* (2013.01); *B01L 3/502761* (2013.01);
(Continued)

(58) Field of Classification Search
CPC ................ C12Q 1/6844; C12Q 1/6853; B01L 2400/043; B01L 2400/0433; B01L 2300/0636
See application file for complete search history.

(56) References Cited

U.S. PATENT DOCUMENTS

2005/0095602 A1    5/2005  West et al.
2020/0025657 A1    1/2020  D'Silva et al.

FOREIGN PATENT DOCUMENTS

WO      WO-2017049279 A1 *  3/2017  .......... B01L 3/50273
WO      2019195818 A1    10/2019
(Continued)

*Primary Examiner* — Young J Kim
(74) *Attorney, Agent, or Firm* — E. Eric Mills; Nicholas P. Stadnyk; Maynard Nexsen PC

(57) ABSTRACT

The invention provides a system and methods of multiplexed, solid-phase isothermal nucleic acid amplification. In various aspects, the invention uses a microfluidic device that includes a field of actuatable microposts in a reaction (or assay) chamber to enhance fluid flow, mixing, and hybridization/capture efficiency in a solid-phase capture assay. In various other aspects, the invention uses oligonucleotide primers immobilized in a field of actuatable microposts in a reaction chamber of a microfluidics device for capture and amplification of target-specific nucleic acids in a sample fluid. The invention provides methods of producing a micropost field (array) on a substrate for printing of a capture array (e.g., an array of primer spots). The invention also provides methods of printing an array of capture spots (e.g., primer spots) on the substrate surface of a micropost field.

25 Claims, 13 Drawing Sheets

(52) U.S. Cl.
CPC ......... *B01L 7/52* (2013.01); *B01L 2200/0652*
(2013.01); *B01L 2200/16* (2013.01); *B01L*
*2300/0636* (2013.01); *B01L 2400/086*
(2013.01)

(56) References Cited

FOREIGN PATENT DOCUMENTS

| WO | 2019221954 A1 | 11/2019 |
| WO | 2020186273 A1 | 9/2020 |

* cited by examiner

100

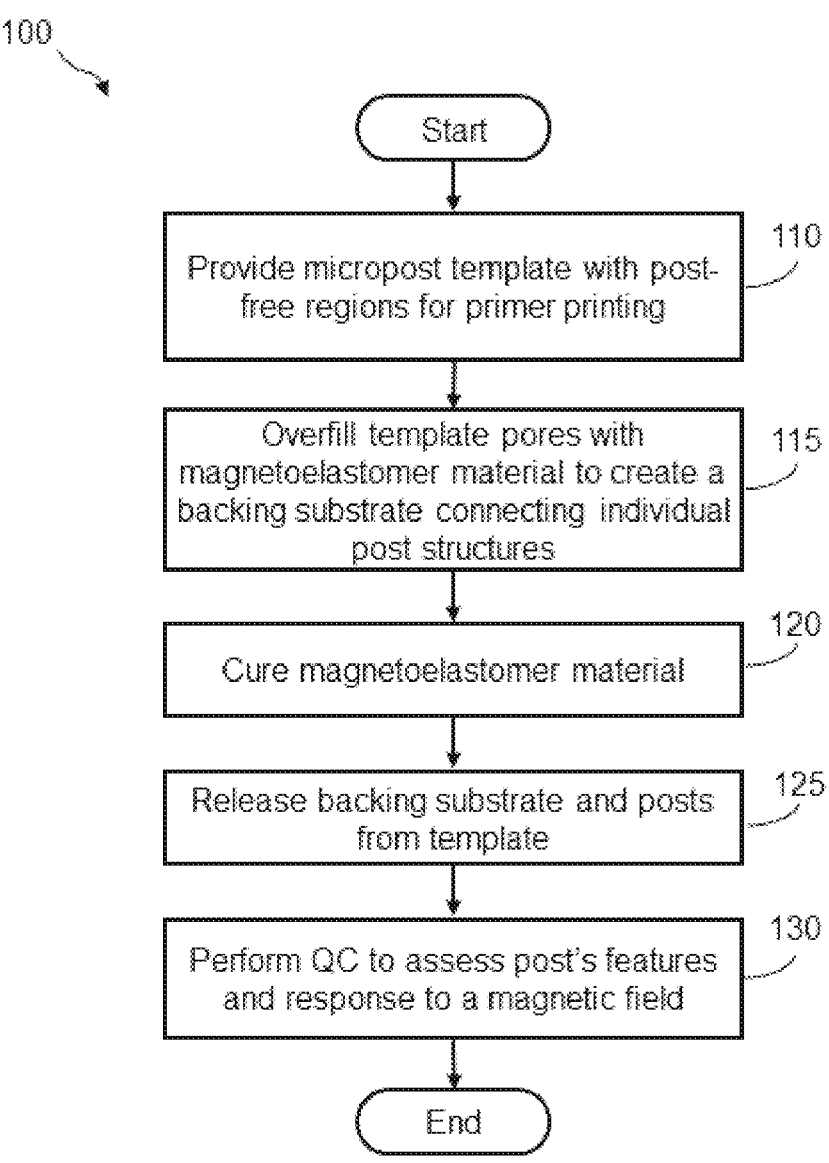

Start

Provide micropost template with post-free regions for primer printing        110

Overfill template pores with magnetoelastomer material to create a backing substrate connecting individual post structures        115

Cure magnetoelastomer material        120

Release backing substrate and posts from template        125

Perform QC to assess post's features and response to a magnetic field        130

End

Influenza A
Influenza B
RSV
SARS-CoV-2
MERS-CoV
Alignment & print control
Positive control
Specificity control

600

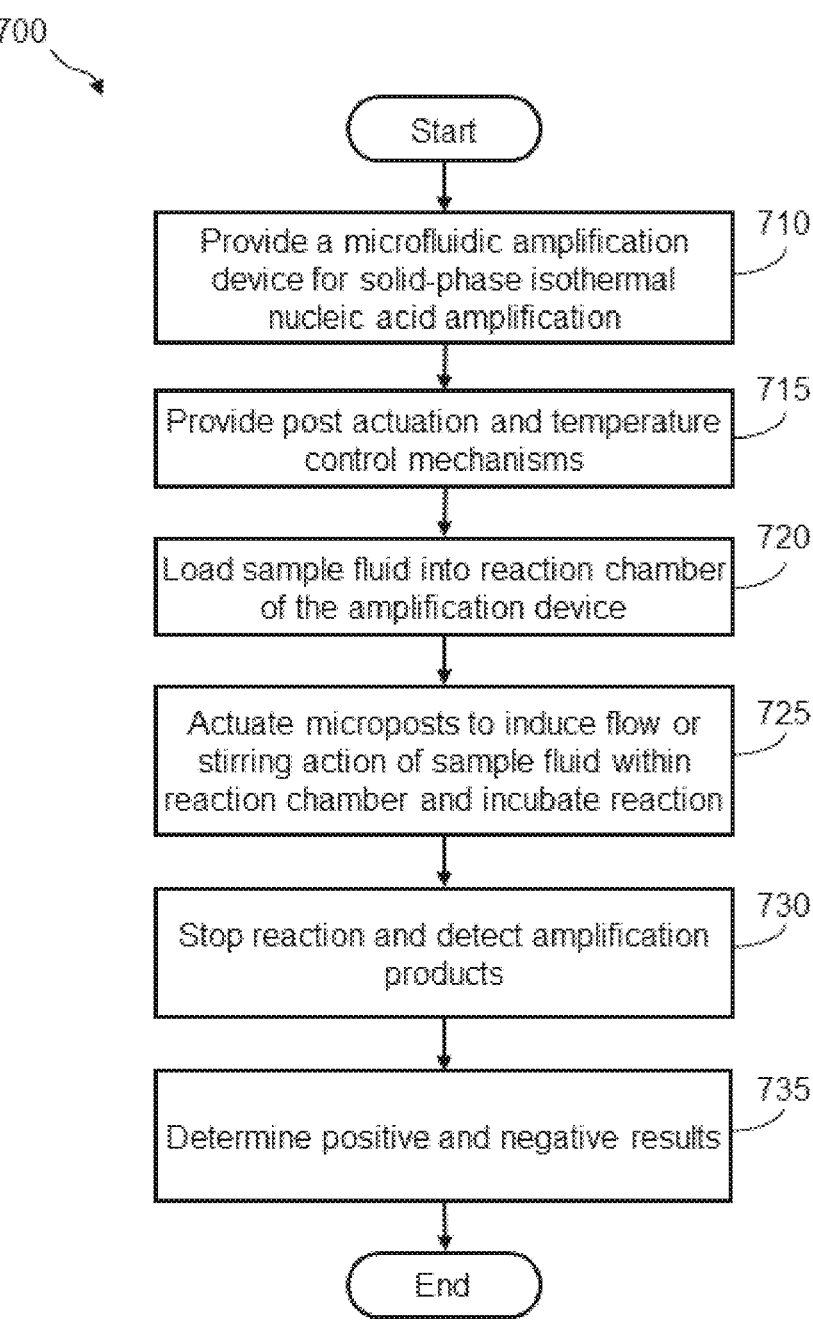

700

Start

Provide a microfluidic amplification device for solid-phase isothermal nucleic acid amplification
710

Provide post actuation and temperature control mechanisms
715

Load sample fluid into reaction chamber of the amplification device
720

Actuate microposts to induce flow or stirring action of sample fluid within reaction chamber and incubate reaction
725

Stop reaction and detect amplification products
730

Determine positive and negative results
735

End

*FIG. 7*

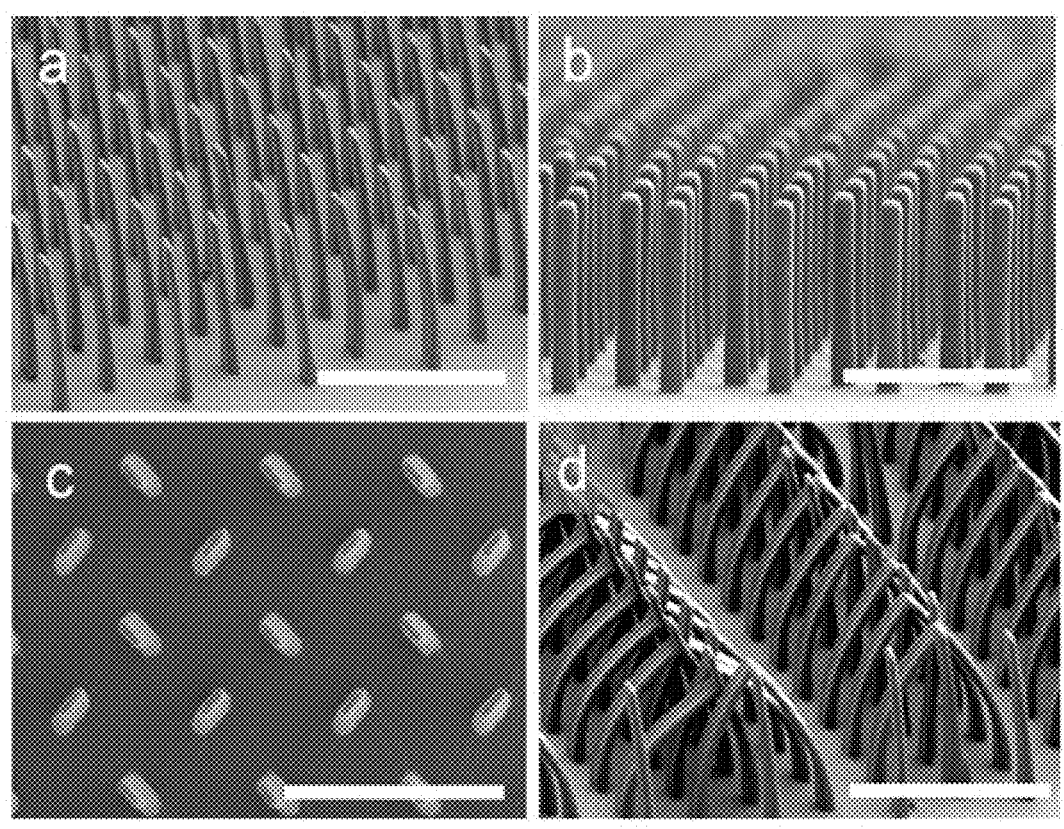
*FIG. 8*

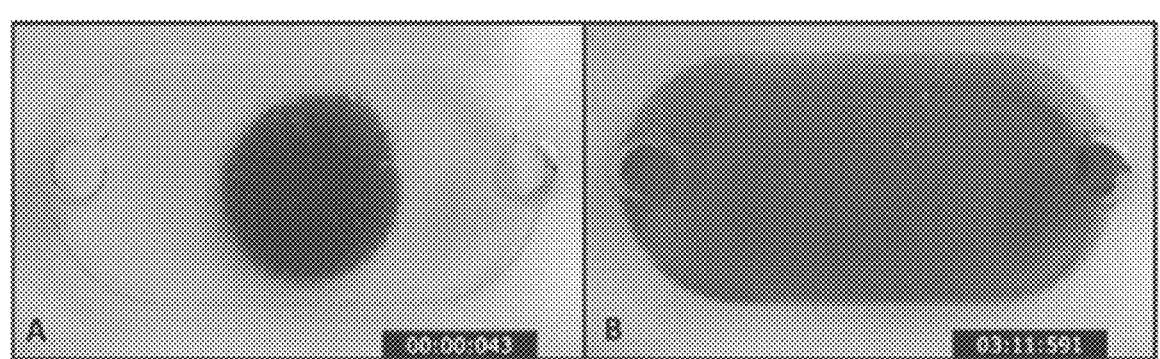
*FIG. 11*

1300

1310

SYSTEM AND METHODS OF USING MICROFLUIDIC AGITATION TO ENHANCE MULTIPLEXED SOLID-PHASE ISOTHERMAL NUCLEIC ACID AMPLIFICATION

RELATED APPLICATIONS

The presently disclosed subject matter is a 35 U.S.C. § 371 U.S. national phase entry of International Application No. PCT/US2021/056836 having an international filing date of Oct. 27, 2021, which claims priority and is related to U.S. Provisional Patent Application No. 63/106,490, entitled "System and Methods of Using Microfluidic Agitation to Enhance Multiplexed Solid-Phase Isothermal Nucleic Acid Amplification," filed on Oct. 28, 2020; the entire disclosure of which is incorporated herein by reference.

TECHNICAL FIELD OF THE INVENTION

The presently disclosed subject matter relates generally to a system and methods of using microfluidic agitation to enhance multiplexed solid-phase isothermal nucleic acid amplification in microfluidic applications.

BACKGROUND

A common theme in infectious disease diagnostics is the need to rapidly differentiate infections requiring quarantine ("Q" infections) from those that do not require quarantine ("non-Q"). Examples of Q infections include filoviruses such as Ebola and Marburg. Examples of non-Q infections include flaviviruses such as Yellow Fever, Typhoid, and Dengue, and *Plasmodia* such as Malaria. Differential diagnosis of patients with non-Q infections will avoid the nosocomial risk of unnecessary quarantine and public health infrastructure will avoid unnecessary burden of putting patients in quarantine who pose little public health risk, while simultaneously enabling proper disease treatment (Mauk, M. G., et al., Biosensors (2018) 8(1): 7; and Obande, G. A. and K. K. Banga Singh, Infection and Drug Resistance (2020) 13: 455-483, which are incorporated herein by reference in its entirety). The ideal differential diagnostic would be fast, highly multiplexed to test for multiple pathogens in a single reaction, and point-of-care (POC)-compatible.

Currently, the gold standard for infectious disease diagnosis is nucleic acid amplification testing (NAAT), owing to its high analytical sensitivity and specificity. The fastest NAATs use isothermal nucleic acid amplification (INAA). Unfortunately, INAA methods struggle with multiplexing. "One-pot" (i.e., in a single reaction) multiplexed INAA is possible for two (2) to three (3) targets, but even this modest level of multiplexing requires significant primer optimization of both sequences to avoid non-specific primer interactions and concentrations to balance unequal amplification kinetics (Lobato, I. M. and C. K. O'Sullivan, Trends in Analytical Chemistry (2018) 98: 19-35; Piepenburg, O., et al., PLOS Biology (2006) 4(7): e204; Kim, J. H., et al., BioChip Journal (2019) 13(4):341-351; and Crannell, Z., et al., Anal Chem (2016) 88(3): 1610-1616, which are incorporated herein by reference in its entirety). Robust INAA at high-plex can only be achieved with spatial encoding to reduce primer interference.

Spatial encoding is typically achieved using a "multi-pot" design, in which isolated chambers incubate the reaction for each target independently. Multi-pot designs require a significant amount of physical space on the test consumable. They also divide the sample into small volumes, such that each reaction well has less analyte to work with; as a result, the limit of detection of the assay suffers as the -plex increases. While pre-amplification can mitigate this limitation, it increases the complexity of the assay, and therefore the cost of the consumable. Solid-phase PCR uses immobilization of one primer or both primers on a surface in a one-pot reaction, while the other reagents remain in solution. Unfortunately, solid-phase PCR efficiency drops as much as 91% compared to solution-phase amplification (Palanisamy, R., Connolly, A. R., and M. Trau, Bioconjugate Chemistry (2010) 21(4): 690-695, which is incorporated herein by reference in its entirety).

There is a need in the art for methods of testing for infectious diseases that are fast, highly multiplexed, cost effective, and point-of care compatible.

SUMMARY OF THE EXEMPLARY EMBODIMENTS

The present invention provides a microfluidic device for nucleic acid amplification.

In one embodiment, the microfluidic device for nucleic acid amplification may comprise a reaction chamber formed between at least two (2) substrates.

In another embodiment, the reaction chamber may further comprise: (i) a micropost field formed on one or more surfaces of the reaction chamber and potentially comprising a plurality of surface-attached actuatable microposts arranged thereon; (ii) a capture probe array wherein the capture probe array may comprise a plurality of capture spots patterned on a reaction surface among the micropost field; and (iii) at least one fluid inlet port and at least one fluid outlet port may be arranged or configured for flowing one or more liquids into and/or out of the reaction chamber.

In certain embodiments, the reaction chamber may have a volume ranging from about 1 $\mu m^2/\mu L$ to about 100 $\mu m^2/\mu L$; from about 1 $\mu m^2/\mu L$ to about 50 $\mu m^2/\mu L$; from about 1 $\mu m^2/\mu L$ to about 25 $\mu m^2/\mu L$; or from about 1 $\mu m^2/\mu L$ to about 10 $\mu m^2/\mu L$.

In another embodiment, the micropost field may be provided on an inner surface of the bottom substrate of the reaction chamber.

In yet another embodiment, the plurality of surface-attached microposts in the micropost field may be arranged to provide regularly spaced post-free regions.

In still another embodiment, the microposts may be layered onto the surface of the chamber using a backing substrate, and wherein the microposts and the backing substrate may comprise a magnetoelastomeric material.

In another embodiment, the surface-attached microposts in the reaction chamber may be configured for actuation in the presence of an actuation force.

In yet another embodiment, one or more of the capture spots may comprise a plurality of immobilized oligonucleotide primers for capture and/or amplification of a target-specific nucleic acid in the sample fluid.

In still another embodiment, the immobilized oligonucleotide primers may comprise a mixture of forward and reverse primers.

In another embodiment, the mixture of forward and reverse primers may be immobilized on a capture spot in proximity sufficient to enable bridge amplification detection of a nucleic acid target.

In yet another embodiment, the capture spots may be positioned within a defined arrangement of surface-attached microposts on a reaction surface.

In another embodiment, the at least one fluid inlet port and the at least one fluid outlet port may be provided in the top substrate of the microfluidic device.

In yet another embodiment, the microfluidic device may further comprise a dried reagent spot on an inner surface, wherein: (a) the dried reagent spot may comprise one or more reagent components for performing a nucleic acid amplification assay; and (b) the dried reagent spot may be selected to be capable of rehydration by a sample fluid in the reaction chamber.

In still another embodiment, the dried reagent spot may be provided on the inner surface of the top substrate of the reaction chamber of the microfluidic device.

In yet another embodiment, the dried reagent spot may comprise one or more reagent components for performing an isothermal amplification reaction.

In still another embodiment, the isothermal amplification reaction may comprise a loop-mediated isothermal amplification (LAMP) assay.

In another embodiment, the isothermal amplification reaction may comprise a recombinase polymerase amplification (RPA) assay.

In still another embodiment, the isothermal amplification reaction may comprise a reverse transcription recombinase polymerase amplification (RT-RPA) assay.

In yet another embodiment, the dried reagent spot may comprise one or more reagent components of a non-isothermal amplification reaction.

In another embodiment, the non-isothermal amplification reaction may comprise a polymerase chain reaction assay (PCR).

The present invention provides a system for nucleic acid amplification.

In one embodiment, the system for nucleic acid amplification may comprise: (a) the microfluidic device of the present invention; (b) an actuation mechanism for applying an actuation force to the reaction chamber of the microfluidic device to actuate movement of at least some of the surface-attached microposts; (c) a temperature control mechanism for maintaining a reaction temperature; and (d) a detection mechanism for detecting amplification products.

In another embodiment, the actuation force may be chosen from a group consisting of a magnetic force, a thermal force, a sonic force, or an electric force.

In still another embodiment, the actuation force may be applied as a function of frequency or amplitude or as an impulse force.

In yet another embodiment, the actuation mechanism may comprise a magnetic drive system.

In another embodiment, the magnetic drive system may comprise a shaft mounted permanent magnet that is driven by a small brushless motor.

In another embodiment, the magnetic drive system may be configured for providing an actuation rate of from about less than 1K RPM to about 20K RPM.

In yet another embodiment, the temperature control mechanism may comprise a high-resolution heat block that is configured to provide temperature control from about 25° C. to about 95° C.

In still another embodiment, the nucleic acid amplification system may further comprise a housing configured for removably receiving the microfluidic device.

The present invention provides a method for producing a micropost field.

In one embodiment, the method for producing a micropost field may comprise the steps of: (a) providing a micropost template, wherein the micropost template may be configured for forming a field of microposts arranged on a backing substrate with micropost-free regions for printing a capture probe array; (b) filling the micropost template with a magnetoelastomeric material, wherein filling the micropost template may comprise overfilling the template thereby forming the backing substrate connecting individual microposts in the micropost field; (c) curing the magnetoelastomeric material; (d) releasing the backing substrate and attached microposts from the micropost template to provide a micropost field on a backing substrate; and (e) performing a quality control process to assess: (i) the features of the microposts; and (ii) the response of the microposts to a magnetic field.

In another embodiment, the micropost template may comprise a plurality of high-aspect pores of sufficient depth to form the micropost structures.

In yet another embodiment, the plurality of pores may be configured for providing: (i) a desired density of surface-attached microposts per area of backing substrate; (ii) a desired cross-sectional micropost shape; and/or (iii) a desired arrangement of surface-attached microposts around one or more capture spots in the capture probe array.

In still another embodiment, the density of surface-attached microposts on the backing substrate may be about $10^4$ posts/cm$^2$.

In another embodiment, the density of surface-attached microposts on the backing substrate may be about $10^5$ posts/cm$^2$.

In yet another embodiment, the density of surface-attached microposts on the backing substrate may be about $10^6$ posts/cm$^2$.

In still another embodiment, the cross-sectional shape of the microposts may be circular.

In another embodiment, the cross-sectional shape of the microposts may be rectangular.

In yet another embodiment, the arrangement of surface-attached microposts around a capture spot may be square in shape.

In still another embodiment, the arrangement of surface-attached microposts around a capture spot may be rectangular in shape.

In another embodiment, the arrangement of surface-attached microposts around a capture spot may be triangular.

In yet another embodiment, the arrangement of surface-attached microposts may be provided as a frame around the capture probe array, thereby providing regions around the capture spots devoid of microposts.

In still another embodiment, the magnetoelastomeric material may comprise a silicon-based elastomeric material.

In another embodiment, the silicon-based elastomeric material may comprise polydimethylsiloxane (PDMS) and a metallic component.

In yet another embodiment, the magnetoelastomeric material may comprise a ferromagnetic-PDMS composite.

In another embodiment, the quality control process may comprise: (a) determining a first quality control metric, wherein the first quality control metric may comprise determining a percentage of upright microposts in the micropost field; (b) determining a second quality control metric, wherein the second quality control metric may comprise determining a percentage of microposts with the targeted feature characteristics; (c) determining a third quality control metric, wherein the third quality control metric may comprise determining a response of the microposts to an actuation force; and (d) determining based on the first, second, and third quality control metrics if the micropost field passes the quality control process.

In yet another embodiment, determining the percentage of upright posts may comprise: (i) collecting one or more images over a defined surface area of a micropost field; (ii) determining the number of upright microposts within the defined area; and (iii) determining the percentage of upright posts in the defined surface area of the micropost field.

In still another embodiment, the defined surface area may be greater than about 10 cm$^2$.

In yet another embodiment, determining the percentage of microposts with the targeted features may comprise: (i) determining the elastic modulus of the microposts; (ii) loading the microposts with material to enable actuation and then measuring a magnetic field produced during actuation of the microposts; (iii) determining the hydrophilicity of the microposts; or (iv) determining the shelf stability of the microposts.

In another embodiment, determining the response of the microposts to an actuation force may comprise measuring a fractional change in intensity of light passing through the micropost field upon actuation of the microposts.

In still another embodiment, the method of producing a micropost field may further comprise performing a capping or blocking process prior to step (b) to block certain regions of the micropost template, thereby defining micropost-free regions on the backing substrate for printing a capture probe array.

In another embodiment, the method of producing a micropost field may further comprise modifying the surfaces of the micropost template to reduce potential adherence of a magnetoelastomeric material to the template during release of the backing substrate and microposts from the template.

In still another embodiment, the method for producing a micropost field may further comprise modifying the composition of a magnetoelastomeric material to reduce potential adherence of the magnetoelastomeric material to the micropost template during release of the backing substrate and microposts.

The present invention provides a method of producing a capture probe array on a substrate surface of a micropost field.

In one embodiment, the method of producing a capture probe array on a substrate surface of a micropost field may comprise the steps of: (a) providing a micropost field on a backing substrate, wherein the micropost field and backing substrate may be formed of a magnetoelastomeric material; (b) modifying the surface of the backing substrate for binding a plurality of oligonucleotide primers; (c) printing an array of oligonucleotide primers on the surface of the backing substrate, thereby providing an array of capture spots that may comprise a plurality of immobilized oligo-nucleotide primers, wherein the plurality of oligonucleotide primers may comprise a plurality of single target specific primers per capture spot, and one or more process controls; (d) performing a quality control process to assess: (i) the features of the primer array; and (ii) target binding.

In another embodiment, the micropost field on a backing substrate may be provided using the method of the present invention.

In still another embodiment, modifying the surface of the backing substrate may comprise treating the surface of the backing substrate with an epoxysilane and the plurality of oligonucleotide primers comprises amino-modified primers.

In yet another embodiment, treating the surface of the backing substrate with epoxysilane may comprise a vapor deposition process.

In another embodiment, treating the surface of the backing substrate with epoxysilane may comprise a low temperature chemical vapor deposition process.

In yet another embodiment, the chemical vapor deposition process may be performed at about 70° C.

In still another embodiment, modifying the surface of the backing substrate may comprise using polyethylene glycol linkers.

In another embodiment, the array of oligonucleotide primers may be printed on micropost-free regions of the backing substrate.

In yet another embodiment, the density (concentration) of single target specific primers may be selected to provide a certain limit-of-detection (LOD) for a diagnostic assay.

In still another embodiment, a concentration of a single target primer printing solution may be from about 0.1 μM to about 100 μM with half-log spacing increments.

In another embodiment, the one or more process controls may comprise a printing control, a fiducial control, a positive control, and/or a specificity control.

In yet another embodiment, the fiducial control may comprise an oligonucleotide with a 5'-Cy5-modification.

In still another embodiment, the positive control may comprise a primer having sequence homology to a synthetic sequence.

In another embodiment, the specificity control may comprise an oligonucleotide having no sequence homology to a target sequence.

In yet another embodiment, the oligonucleotide primers may be immobilized onto the backing substrate surface from the 5'-end of the molecule.

In still another embodiment, the array of immobilized oligonucleotide primers may comprise a 5×10 primer array of about 12.5 mm$^2$ in total array area.

In another embodiment, the 5×10 primer array may comprise a plurality of capture spots of about 100 μm in diameter with a pitch of about 400 μm.

In yet another embodiment, the array of oligonucleotide primers may comprise a multiplexed array for detecting target nucleic acids from a panel of respiratory pathogens.

In still another embodiment, the panel of respiratory pathogens may comprise SARS-CoV-2, influenza A, influenza B, respiratory syncytial virus (RSV), and MERS-CoV.

In yet another embodiment, the multiplexed array may comprise a 125-plex array with 10 capture spots per a pathogen target nucleic acid.

In another embodiment, the 125-plex array may comprise a 5×10 array with a capture spot density of about 25 target capture spots per mm$^2$.

In yet another embodiment, the array of immobilized oligonucleotide primers may be printed using a non-contact printing method.

In still another embodiment, the array of immobilized oligonucleotide primers may be printed using a contact printing method.

In another embodiment, contact printing parameters may be selected to provide less than about a 10% variance in the features of the primer array.

In yet another embodiment, the quality control process may comprise: (a) hybridizing a plurality of labeled oligo-nucleotide sequences that may be complementary to the target specific primers on the capture probe array, wherein binding of the labeled oligonucleotide sequence to a target specific primer may provide a detection signal; (b) washing the capture probe array to remove non-hybridized labeled oligonucleotide sequences; (c) scanning the capture probe array to detect a signal from the labeled oligonucleotide sequences bound to the target specific primers at each capture spot; (d) calculating the average capture spot signal intensity and standard deviation in intensities; (e) determining based on the average capture spot signal intensity and standard deviation if the capture probe array passes the quality control process.

In still another embodiment, the labeled oligonucleotide may comprise a fluorescently labeled oligonucleotide.

In another embodiment, a capture probe array with less than about 10% variance in feature size and detection signal may be determined as passing the quality control process.

The present invention provides a method of amplifying a target nucleic acid in a sample fluid.

In one embodiment, the method of amplifying a target nucleic acid in a sample fluid may comprise the steps of: (a) providing the microfluidic device and system according to the present invention; wherein either (i) a capture spot in the capture array of the microfluidic device may comprise target specific forward and reverse primers immobilized thereon or (ii) a capture spot in the capture array of the microfluidic device may comprise target specific forward primers immobilized thereon, and the reverse primer may be provided in a sample fluid; (b) providing a reaction temperature; wherein the reaction temperature may be selected for detecting a target nucleic acid in the sample fluid; (c) introducing the sample fluid that may potentially comprise a target nucleic acid into the reaction chamber of the microfluidic device; (d) actuating the micropost field of the microfluidic device to induce a flowing or stirring or mixing action of the sample fluid within the reaction chamber, thereby facilitating hybridization of a target nucleic acid in the sample fluid to potentially capture a spot in the capture probe array and initiating an amplification reaction; (e) stopping the amplification reaction; (f) detecting an amplification product, wherein the detecting may comprise measuring a detection signal, thereby providing a measurement for assessing the presence of a target nucleic acid; and (h) determining based on the measured detection signal if a target nucleic acid may be present.

In certain embodiments, the stopping of the amplification process may comprise (i) removing the sample fluid from the reaction chamber of the microfluidic device after an incubation period and (ii) washing the capture probe array to remove non-hybridized reaction components.

In certain other embodiments, the detecting of an amplification product may comprise either (i) a detection solution that may comprise a nucleic acid dye is introduced into the reaction chamber of the microfluidic device, wherein binding of the nucleic acid dye to amplification products bound at a capture spot may produce a detection signal or (ii) a fluorescence modification of a reverse primer may be provided in the sample fluid may be used to provide a detection signal.

In another embodiment, the reaction temperature may be selected to optimize performing an isothermal amplification reaction.

In yet another embodiment, the temperature for performing an isothermal amplification reaction may be from about 25° C. to about 38° C.

In still another embodiment, the temperature for performing an isothermal amplification reaction may be from about 25° C. to about 65° C.

In another embodiment, the temperature may be selected to optimize performing a non-isothermal amplification reaction.

In still another embodiment, the temperature for performing a non-isothermal amplification reaction may be selected for thermal cycling in a range from about 40° C. to about 95° C.

In yet another embodiment, the temperature may be selected to optimize hybridization of target amplification products to the capture probe array.

In another embodiment, the hybridization temperature may be from about 40° C. to about 45° C. for RPA and from about 60° C. to about 70° C. for LAMP.

In still another embodiment, the sample fluid may further comprise one or more reaction components for amplification of a target nucleic acid in the sample fluid.

In yet another embodiment, the reaction components may comprise target specific forward and reverse primers and amplification reagents for a solution-phase amplification reaction.

In another embodiment, the reaction components may comprise target specific reverse primers and amplification reagents for a solid-phase amplification reaction.

In still another embodiment, the reaction components may comprise reaction components for a bridge solid-phase amplification reaction.

In certain embodiments, the incubation period may be about five (5) minutes or less; about fifteen (15) minutes or less; about thirty (30) minutes or less; or about sixty (60) minutes or less.

In another embodiment, washing the capture probe array to remove non-hybridized reactants and artifacts may comprise rinsing the reaction chamber with a wash solution.

In still another embodiment, the wash solution may comprise 0.1×SSC and PBS.

In yet another embodiment, the nucleic acid dye may comprise a fluorescent nucleic acid dye.

In still another embodiment, the fluorescent nucleic acid dye may comprise an intercalating dye.

In another embodiment, the intercalating dye may comprise SYBR Green.

In yet another embodiment, the fluorescence modification of a reverse primer may comprise a 5'-Cy5-modification.

In still another embodiment, measuring the detection signal may comprise: (a) scanning the capture array for a detection signal, wherein the detection signal may comprise a fluorescence signal; (b) determining fluorescence at an excitation/emission wavelength selected based on the nucleic acid dye or reverse primer fluorescent modification; and (c) producing a measurement for assessing the presence of a target nucleic, wherein the measurement may comprise calculating an average capture spot signal intensity and standard deviation in intensities.

In another embodiment, the method of amplifying a target nucleic acid in a sample fluid may further comprise providing a dried reagent spot on an inner surface of the reaction chamber of the microfluidic device, wherein the dried reagent spot may comprise reagents for a solid-phase isothermal amplification reaction.

In still another embodiment, the microfluidic device may comprise a capture array configured for detecting target nucleic acids from a panel of respiratory pathogens.

In yet another embodiment, the panel of respiratory pathogens may comprise SARS-CoV-2, influenza A, influenza B, respiratory syncytial virus (RSV), and MERS-CoV.

Other compositions, methods, features, and advantages of the invention will be or will become apparent to one with skill in the art upon examination of the following figures and detailed description. It is intended that all such additional compositions, methods, features, and advantages be included within this description, be within the scope of the invention, and be protected by the accompanying claims.

BRIEF DESCRIPTION OF THE DRAWINGS

The features and advantages of the present invention will be more clearly understood from the following description taken in conjunction with the accompanying drawings, which are not necessarily drawn to scale, and wherein:

FIG. 1 is a flow diagram illustrating an example of a method of producing a micropost field on a substrate with post-free regions for printing of a capture array (e.g., primer array).

FIG. 7 is a flow diagram illustrating an example of a method of testing for a panel of infectious pathogens in a single solid-phase nucleic acid amplification assay.

FIG. 8 is a panel of scanning electron microscope images showing soft magnetically actuatable microposts created using different templates.

FIG. 11 is a pair of screenshots of an example of rehydrating a dried reagent spot in a microfluidic amplification device.

DETAILED DESCRIPTION OF THE INVENTION

Figure 2:
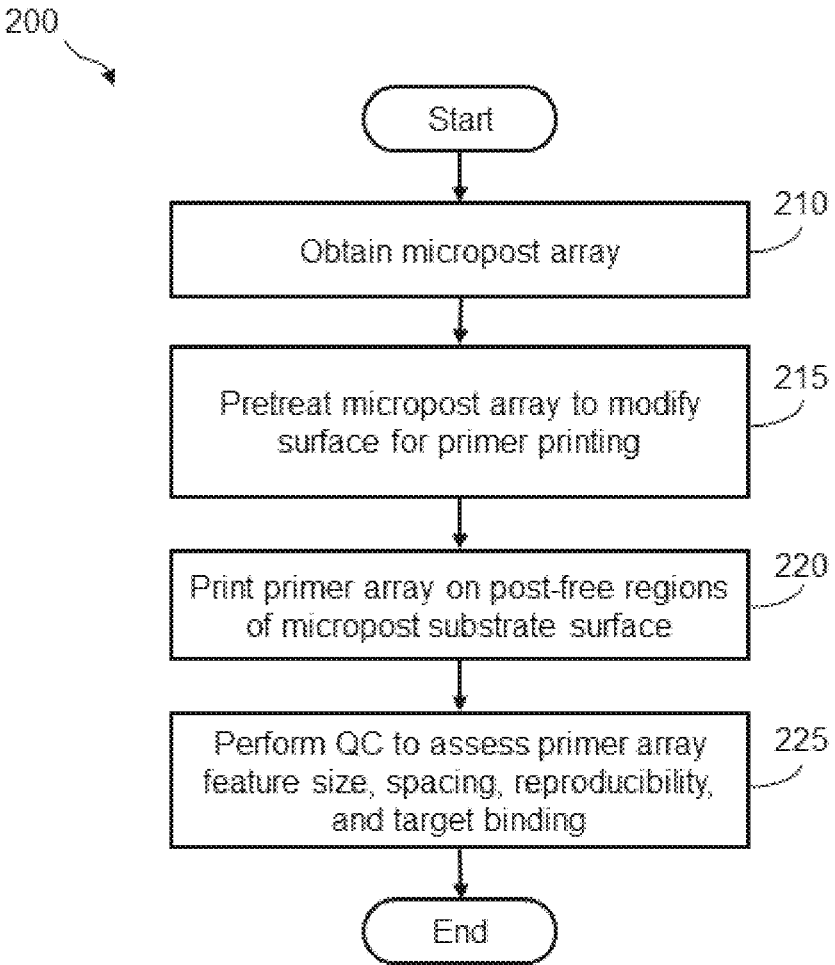
FIG. 2 is a flow diagram illustrating an example of a method of printing a primer array on a micropost substrate surface.

The presently disclosed subject matter now will be described more fully hereinafter with reference to the accompanying drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

The invention provides a system and methods of multiplexed, solid-phase isothermal nucleic acid amplification. In various aspects, the invention uses a microfluidic device that includes a field of actuatable microposts in a reaction (or assay) chamber to enhance fluid flow, mixing, and hybridization/capture efficiency in a solid-phase capture assay.

In various aspects, the invention uses oligonucleotide primers immobilized in a field of actuatable microposts in a reaction chamber of a microfluidics device for capture and amplification of target-specific nucleic acids in a sample fluid.

The invention provides methods of producing a micropost field (array) on a substrate for printing of a capture array (e.g., an array of primer spots).

In some aspects, a micropost field (array) on a substrate includes post-free regions for printing of a capture array (e.g., an array of primer spots).

The invention provides methods of printing an array of capture spots (e.g., primer spots) on the substrate surface of a micropost field.

In some embodiments, an array of capture spots (e.g., primer spots) are printed on the substrate surface in regions that are devoid (absent) of posts.

In one aspect, the invention integrates actuatable microposts, a primer array, and isothermal amplification reagents in an "all-in-one" amplification device (module) that can be bonded into a microfluidics cartridge.

The invention is useful for rapid, sensitive, and highly multiplexed testing for a panel of infectious pathogens in a single diagnostic nucleic acid amplification assay at a point-of-care setting. The flexibility in printing multiple target-specific capture spots (e.g., target-specific primer spots) onto a substrate surface of a microfluidic device allows for expanded and/or new infectious disease testing panels to be readily provided.

Microposts

The invention uses a field of actuatable microposts in a reaction or assay chamber to enhance fluid flow, mixing, and hybridization/capture efficiency in solid-phase capture assay. Various parameters of a micropost field can be selected to enhance the performance (e.g., fluid flow, mixing, and capture efficiency) and/or compatibility with same-surface printing methods for printing a capture array (e.g., an oligonucleotide primer array).

In one aspect, the micropost field occupies a frame around the printed capture array, e.g., primer spots in the array are separated by regions without posts.

In one aspect, the density of posts in a micropost field is about $10^4$ posts/cm$^2$ (low density).

In one aspect, the density of posts in a micropost field is about $10^5$ posts/cm$^2$ ("standard" density).

In one aspect, the density of posts in a micropost field is about $10^6$ posts/cm$^2$ (high density).

In one aspect, the post arrangement around a capture spot (e.g., a primer spot) in an array is square in shape.

In one aspect, the post arrangement design around a capture spot (e.g., a primer spot) in an array is rectangular in shape.

In one aspect, the post arrangement around a capture spot (e.g., a primer spot) in an array is triangular in shape.

In one aspect, the cross-sectional shape of the microposts is circular.

In one aspect, the cross-sectional shape of the microposts is rectangular (i.e., rectangular cross section posts (RCSP)). Because of their preferred bending direction, RCSP micropost arrays can be arranged in higher densities along their "stiff" axis direction without danger of post-post stiction. Higher post density will create higher fluid flow and mixing. An RCSP array design can also be used to create a phase difference in beating for adjacent posts.

In one aspect, a template (or mold) is used to produce a micropost field on a "backing" substrate with regularly spaced post-free regions. The template includes, for example, a plurality of deep, high-aspect pores that will form the micropost structures. A template can be created to provide, for example, a certain post density; cross-sectional post shape; and arrangement of post regions relative to printing regions (i.e., primer spots).

In one aspect, a "standard" template (or mold) with a post density of about $10^5$ posts/cm$^2$ and circular cross section posts is used to produce a micropost field, wherein a capping or blocking process is used to block regions of the template and define post-free zones for printing capture spots (e.g., primer spots).

In various aspects, a micropost field on a "backing" substrate is formed of a magnetoelastomeric material.

In one aspect, the surfaces of a template (or mold) can be modified to reduce the tendency of a magnetoelastomeric material to stick to the template during release of the micropost substrate from the template.

In one aspect, the composition of the magnetoelastomeric material can be modified to reduce the tendency of the material to stick to the template during release of the micropost substrate from the template.

FIG. 1 is a flow diagram illustrating an example of a method 100 of producing a micropost field on a substrate with post-free regions for printing of a capture array (e.g., primer array). Method 100 may include any or all the following steps as well as additional unspecified steps.

At a step 110, a micropost template (or mold) configured to produce a micropost field on a substrate with regularly spaced post-free regions is provided. The template includes, for example, a plurality of deep, high-aspect pores that will form the micropost structures. A template is selected to provide, for example, a certain post density; cross-sectional post shape; and arrangement of posts relative to printing regions (i.e., primer spots).

At a step 115, the template is overfilled with a magnetoelastomer material. In one example, the magnetoelastomer material is a ferromagnetic-PDMS composite. Overfilling the template pores with the magnetoelastomer material creates a "backing" substrate connecting individual post structures into a single field of microposts with the selected features.

At a step 120, the magnetoelastomer material is cured.

At a step 125, the microposts and backing substrate are released from the template. For example, the backing substrate is peeled off from the template, releasing the backing substrate and microposts.

At a step 130, a quality control (QC) process is performed to assess micropost features and response to a magnetic field. For example, a first QC metric is the percentage of upright posts (i.e., not knocked down or otherwise damaged) in the micropost field. The percentage of upright posts is determined by collecting images over a large surface area (e.g., greater than about 10 cm$^2$), i.e., [(#upright posts)/(#template features)]×100=% upright. Greater than about 90% upright posts are expected. A second QC metric is the number of posts with the targeted shape and diameter. A third QC metric is the response (e.g., tilt angle) of the microposts to an actuation force. For example, the response of the posts to a known magnetic field strength is determined by measuring the fractional change in the intensity of light passing through the post array. More responsive (i.e., farther tilted) posts create a larger change in transmitted light. An actuation amplitude of about greater than 450 is expected. More responsive posts are known to generate better mixing.

Other methods or ways of determining the percentage of microposts with the targeted features include: (i) determining the elastic modulus of the microposts, e.g., by elongation, indentation, or shear; (ii) loading of the microposts (individually or in the aggregate) with material to enable actuation (e.g., magnetically-permeable material for magnetic actuation, a dielectric for capacitive actuation, or a conductor for electric actuation), wherein a measuring means, such as a superconducting quantum interference device (SQUID), is used to measure the resulting (weak) magnetic field produced by the "loaded" microposts during actuation (note that SQUIDs are currently known to be capable of measuring magnetic fields as low as 5 aT ($5 \times 10^{-18}$ T)); (iii) hydrophilicity of the microposts, which can be measured by contact angle (potentially as a function of time); or (iv) shelf stability of the microposts (also as a function of time since fabrication of the microposts).

Primer Array

The invention uses an array of capture sites patterned on a reaction surface among an array or field of actuatable microposts.

In various aspects, the invention uses an array of immobilized oligonucleotide primers as capture probes to bind one or more nucleic acid targets in a sample fluid.

The size (e.g., primer spot diameter) and pitch (distance between primer spots) of the features in the array can be varied. In one aspect, a primer array is a 5×10 array of 100 µm diameter spots with a 400 µm pitch (i.e., total array area=12.5 mm$^2$).

The type of primer (i.e., forward and/or reverse primer) printed on the array can be varied.

In one aspect, the primer spots on the substrate surface include forward (sense) primers only and the corresponding reverse primers are provided in an amplification reagent solution.

In one aspect, the primer spots on the substrate surface include both forward (sense) and reverse (antisense) primers that are immobilized in close proximity. Printing both forward and reverse primers in close proximity in a primer spot allows for bridge amplification.

As used herein, "forward" primers mean "sense" primers and "reverse" primers mean "anti-sense" primers. That is, forward primers anneal to the anti-sense strand of double-stranded DNA, which runs from the 3' to 5' direction, whereas reverse primers anneal to the sense strand of double-stranded DNA, which runs from the 5' to 3' direction. Furthermore, "5' primers" refer to forward primers, while "3' primers" refer to reverse primers.

Forward and reverse primers are the two types of primers used in the PCR (polymerase chain reaction) to amplify a specific part of a DNA strand.

The density of primers in the array spots can vary. In one aspect, the concentration of a single target primer in a primer-printing solution used to print the array can be varied. For example, a single target primer-printing solution can be from about 0.1 μM to about 100 μM with half-log spacing increments.

In one aspect, the density (concentration) of immobilized primers can be selected to provide a certain limit-of-detection (LOD) for a diagnostic assay.

A printed primer array can include one or more "process" controls. For example, a printed array can include a printing and fiducial control (e.g., an oligonucleotide with a 5'-Cy5-modification); a positive control (i.e., primers with sequence homology only to a synthetic sequence); and a specificity control (e.g., an oligonucleotide with no sequence homology).

The number of intended targets (i.e., "plex") represented on the array can be varied. In one aspect, a 125-plex array with ten (10) primer spots per disease is formed in a 5×10 array with a spot density of about twenty-five (25) target spots per mm² (i.e., 1,250 spots in the array).

The flexibility in printing multiple target-specific primers onto a substrate surface allows for expanded and/or new testing panels to be readily provided.

In one aspect, a non-contact printing method is used to pattern an array of primer spots on the substrate surface of a micropost field in regions that are devoid (absent) of posts. The oligonucleotide primers are immobilized onto the substrate surface from the 5'-end. The substrate surface can be modified prior to printing the array to enhance binding of the primers to the substrate surface. In one example, pretreatment of a substrate surface formed of a silicone-based elastomer (e.g., PDMS) with an epoxysilane (via vapor deposition) can be used to enhance binding of amino-modified primers to the substrate surface. In another example, a relatively low temperature (approximately 70° C.) chemical vapor deposition (CVD) process can be used to modify the substrate surface prior to printing an array of primer spots.

In one aspect, a contact printing (stamping) method is used to pattern an array of primer spots on the substrate surface of a micropost field in regions that are devoid of posts. For example, alignment fiducials on a primer array stamp and a micropost field array are used to align the primer array with regions on the micropost field that are devoid of posts. The substrate surface can be modified prior to printing the array to enhance binding of the primers to the substrate surface. In one example, a substrate surface can be modified using polyethylene glycol (PEG) linkers to project primers above the substrate surface. Printing pressure and contact time can be selected to provide printed arrays with high reproducibility in feature size (i.e., less than about 10% variance) and fluorescent signal (i.e., less than about 10% variance).

FIG. 2 is a flow diagram illustrating an example of a method 200 of printing a primer array on a micropost substrate surface. Method 200 may include any or all the following steps as well as additional unspecified steps.

At a step 210, a micropost array is obtained. In one example, the micropost array is formed of a silicone-based elastomer.

At a step 215, the micropost array is pretreated to modify the surface for primer printing. In one example, micropost array with an epoxysilane (via vapor deposition) for printing with amino-modified oligonucleotide primers.

At a step 220, a primer array is printed on the post-free regions of the micropost substrate surface. In one example, the primer array is printed using a non-contact printing method. The primers are immobilized on the substrate surface from the 5'-end. In one example, a primer array is a 5×10 array of 100 μm diameter spots with a 400 μm pitch (i.e., total array area=12.5 mm²).

In a step 225, a quality control (QC) process is performed to assess primer array features and target binding. For example, array printing is evaluated via fluorescence detection of labeled sequences that are complementary to the printed primer(s). Sequences are hybridized with the primers for about two (2) hours at room temperature, followed by a wash step to remove non-hybridized molecules. The micropost array with printed primer array thereon is scanned using an Olympus IX83 inverted microscope with a motorized translation stage. The data is then analyzed to determine the average spot intensity and standard deviation in intensities. Printed arrays with high reproducibility in feature size (i.e., less than about 10% variance) and fluorescent signal (i.e., less than about 10% variance) are considered acceptable.

Solid-Phase Amplification Assays

The invention uses a nucleic acid amplification assay for amplification of target nucleic acids in a sample fluid.

In some embodiments, a non-isothermal amplification assay is used to amplify target nucleic acids in a sample fluid.

In one embodiment, the non-isothermal amplification assay used to amplify target nucleic acids in a sample fluid is a polymerase chain reaction (PCR) assay.

In some embodiments, an isothermal amplification assay is used to amplify target nucleic acids in a sample fluid.

In one embodiment, the isothermal amplification assay used to amplify target nucleic acids in a sample fluid is a loop-mediated isothermal amplification (LAMP) assay.

In one embodiment, the isothermal amplification assay used to amplify target nucleic acids in a sample fluid is a recombinase polymerase amplification (RPA) assay.

The RPA assay is well known in the art for its low power requirements (37-42° C.), fast time-to-result (<fifteen (15) minutes), and compatibility with lyophilization (Lillis, L., et al., PLOS ONE (2014) 9(9): e108189; Yeh, E.-C., et al., Science Advances (2017) 3(3): e1501645; and Mauk, M., et al., Lab on a Chip (2017) 17(3): 382-394, which are incorporated herein by reference in its entirety). The RPA assay has also been demonstrated to be advantageous for spatially resolved multiplexed amplification (Kersting, S., et al., Mikrochim Acta (2014) 181(13-14): 1715-1723; and Jauset-Rubio, M., et al., Analytical and Bioanalytical Chemistry (2017) 409(1): 143-149, which are incorporated herein by reference in its entirety). In one example, TwistDx™ isothermal amplification reagents are used.

In various aspects, the invention uses a reverse transcription recombinase polymerase amplification (RT-RPA) assay for detection of one or more RNA and/or DNA targets in a sample fluid. The RT-RPA assay is well known in the art for detection of viral RNAs (Behrmann, O., et al., Clinical Chemistry (2020) May 8: hvaa116, which is incorporated herein by reference in its entirety). In one example, TwistDx™ isothermal amplification reagents reverse transcription and amplification are used.

The incubation time for a solid-phase RPA assay can be selected to provide sufficient time to generate an acceptable signal (i.e., signal-to-noise ratio>three (3)). For example, the incubation time may be about sixty (60) minutes or less; or about thirty (30) minutes or less; or about fifteen (15) minutes or less; or about five (5) minutes or less.

In various aspects, the hybridization temperature is from about 40° C. to about 45° C. for RPA and from about 60° C. to about 70° C. for LAMP.

In various aspects, an amplification assay for detecting target nucleic acids in a sample fluid is a "hybrid" amplification assay, wherein a reaction solution or a portion of a reaction solution is set-up in a microtube on-bench and then loaded into a reaction chamber of a microfluidic amplification device.

In one aspect, a hybrid amplification assay is a solution-phase assay wherein all assay components (e.g., target-specific forward and reverse primers, sample, and assay reagents) are combined in a reaction solution and incubated on-bench. The amplification reaction is then evaluated by loading the reaction solution onto the hybridization surface of a microfluidic amplification device. After an incubation period sufficient for amplicon binding to primer sites, a wash step is performed to remove non-hybridized molecules. The hybridization surface (primer array) is then scanned using an Olympus IX83 inverted microscope with a motorized translation stage and the data is then analyzed to determine the average spot intensity and standard deviation in intensities. In one example, the concentration of forward and reverse primers in a solution-phase assay about 420 nM.

In one aspect, a hybrid amplification assay is a solid-phase assay wherein target-specific forward primers are immobilized on a hybridization surface in the reaction chamber of the amplification device and other assay components (e.g., corresponding reverse primer, sample, and assay reagents) are combined on-bench in a reaction solution and then loaded into the reaction chamber of the device. The amplification reactions with reverse primers in solution-phase are detected, for example, using a 5'-Cy5'-fluorescence modification to the reverse primer. After amplification, the hybridization surface (primer array) is scanned using an Olympus IX83 inverted microscope with a motorized translation stage and the data is then analyzed to determine the average spot intensity and standard deviation in intensities. In one example, the forward primer is immobilized on the hybridization surface at a concentration ranging from about 0.1 μM to about 100 μM and the reverse primer is provided in the reaction solution at a concentration of 420 mM.

In one aspect, a hybrid amplification assay is a "bridge" solid-phase assay wherein target-specific forward and reverse primers are immobilized in close proximity on a hybridization surface in the reaction chamber of the amplification device and other assay components (e.g., sample and assay reagents) are combined on-bench in a reaction solution and then loaded into the reaction chamber of the device. After amplification, the hybridization surface (primer array) is scanned using an Olympus IX83 inverted microscope with a motorized translation stage and the data is analyzed to determine the average spot intensity and standard deviation in intensities. In one example, forward and reverse primers are immobilized on the hybridization surface at a 1:1 ratio at concentrations ranging from about 0.1 μM to about 100 μM.

In one aspect, reagents for a solid-phase RPA assay are provided on an inner surface of an amplification device as a dried reagent "master mix". The dried reagent master mix is readily rehydrated when a sample is introduced into the reaction chamber of the device.

Device

Figure 3A:
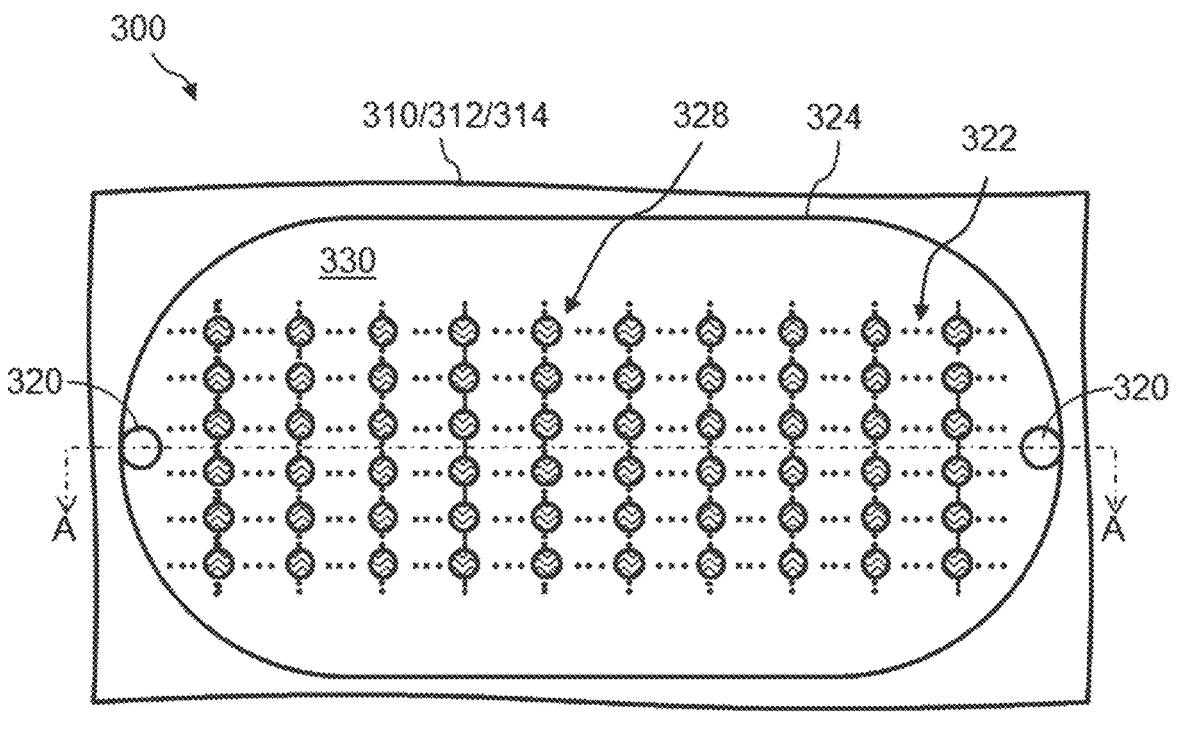
FIG. 3A and FIG. 3B are a plan view and a cross-sectional view, respectively, illustrating an example of a microfluidic amplification device that includes a reaction (or assay) chamber, wherein the reaction chamber includes alternating regions of microposts and immobilized oligonucleotide primers.
Figure 3B:
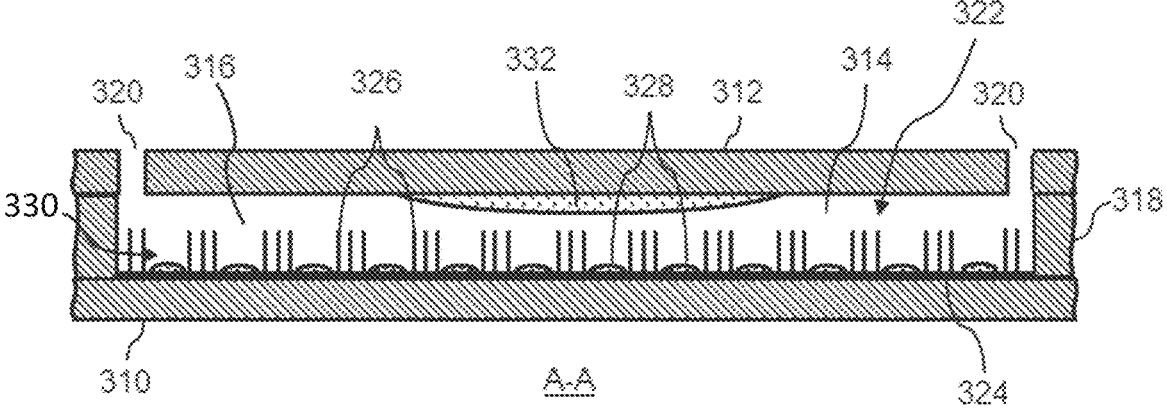

FIG. 3A and FIG. 3B are a plan view and a cross-sectional view, respectively, illustrating an example of a microfluidic amplification device 300 that includes a reaction (or assay) chamber, wherein the reaction chamber includes alternating regions of microposts and immobilized oligonucleotide primers. FIG. 3B is a cross-sectional view taken along line A-A of FIG. 3A.

In this example, amplification device 300 includes a bottom substrate 310 and a top substrate 312 separated by a gap 314, thereby forming a reaction (or assay) chamber 316. A spacer or gasket 318 may be provided between bottom substrate 310 and top substrate 312 to form gap 314 and define the area of reaction chamber 316. Bottom substrate 310 and top substrate 312 can be formed, for example, of plastic or glass. Loading ports 320 are provided, for example, in top substrate 312. For example, two (2) loading ports 320 are provided, one at each end (e.g., an inlet and an outlet) for supplying liquid into or out of reaction chamber 316. In this example, amplification device 300 provides a simple "flow cell" type of chamber comprising a solid surface across which one or more liquids can be flowed, wherein the chamber has at least one inlet and at least one outlet.

Reaction chamber 316 of amplification device 300 can be sized to hold any volume of liquid. The height (i.e., surface area to volume ratio) of gap 314 of reaction chamber 316 can be, for example, from about 1 $\mu m^2/\mu L$ or about 3 $\mu m^2/\mu L$ (standard) or about 6 $\mu m^2/\mu L$. Various fluidic operations such as, but not limited to, mixing, binding, and washing operations can take place within reaction chamber 316.

A micropost field 322 on a substrate 324 is provided on the inner surface of bottom substrate 310. Microposts field 322 includes a plurality of surface-attached microposts 326 arranged on substrate 324 to provide regularly spaced post-free regions. Each micropost 326 includes a proximal end attached to substrate 324 and a distal end that extends into gap 314. Accordingly, the distal ends of micropost 326 extend into a sample fluid (not shown) that can be loaded into reaction chamber 316.

Substrate 324 and microposts 326 are formed, for example, of a magnetically responsive silicone-based elastomer material (i.e., a magnetoelastomer). In one example, substrate 324 and microposts 326 are formed of polydimethylsiloxane (PDMS) and a metallic component. The density of microposts 326 on substrate 324 can be varied. In one example, the density of microposts 326 on substrate 324 is about $10^5$ posts/cm². The length, diameter, and cross-sectional shape of microposts 326 can be varied. For example, the length of microposts 326 can be from about 1 μm to about 100 μm. The diameter of microposts 326 can be from about 0.1 μm to about 10 μm. The cross-sectional shape of microposts 326 can be, for example, circular or rectangular. In one example, microposts 326 are cylindrically shaped and about 4 μm in diameter and about 50 μm in height.

Micropost field 322 on substrate 324 is based on, for example, the microposts described in the U.S. Pat. No. 9,238,869, entitled "Methods and systems for using actuated surface-attached posts for assessing biofluid rheology," issued on Jan. 19, 2016; the entire disclosure of which is incorporated herein by reference. The '869 patent describes methods, systems, and computer readable media for using actuated surface-attached posts for assessing biofluid rheology. An actuation force is generated in proximity to the micropost array that compels at least some of the microposts 326 to exhibit motion. As used herein, the term "actuation force" refers to the force applied to the microposts 326. For example, the actuation force may include a magnetic, thermal, sonic, or electric force. Notably, the actuation force may be applied as a function of frequency or amplitude, or as an impulse force (i.e., a step function). Microposts 326 can be actuated into movement via an actuation force as described in more detail with reference to FIG. 4.

An array of primer spots 328 is printed on substrate 324 in regions that are devoid of microposts 326 to form a hybridization surface 330. In one example, primer spots 328 include a mixture of forward and reverse oligonucleotide primers that are immobilized on the surface of substrate 324 from the 5'-end. Each primer spot 328 or group(s) of primer spots 328 can include oligonucleotide primers that are specific for different target analytes.

A dried reagent spot 332 is provided on the inner surface of top substrate 312. In one example, dried reagent spot 332 reagents (e.g., enzymes, buffer, dNTPs) for the isothermal Recombinase Polymerase Amplification (RPA) assay. Dried reagent spot 332 can be readily rehydrated, for example, by flowing a sample fluid into reaction chamber 316 via loading port 320.

Figure 4:
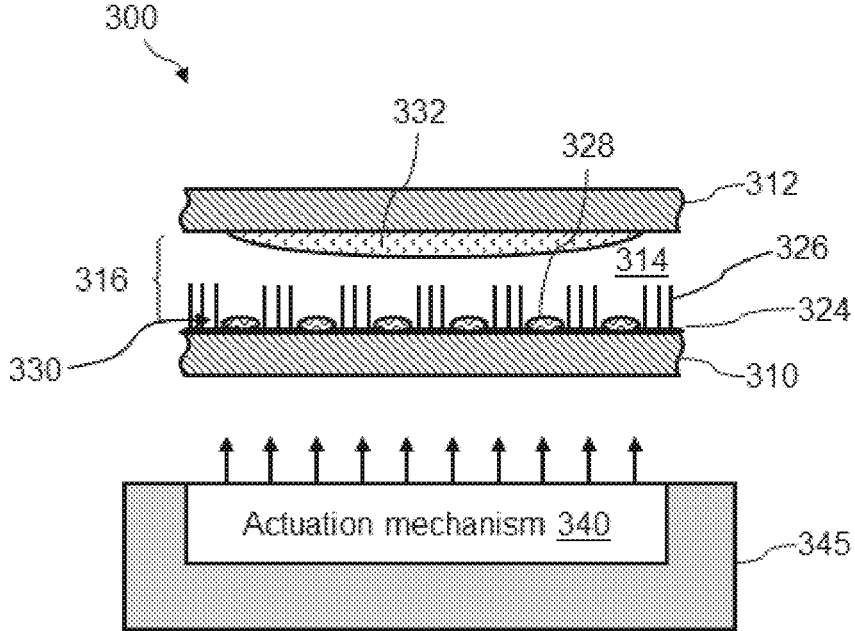
FIG. 4 is a side view illustrating a portion of the reaction chamber in the amplification device of FIG. 3 and shows an actuation mechanism arranged in close proximity to the reaction chamber.

FIG. 4 is a side view illustrating a portion of reaction chamber 316 of amplification device 300 of FIG. 3 and shows an actuation mechanism 340 arranged in close proximity to reaction chamber 316. Actuation mechanism 340 can be any mechanism for actuating microposts 326 of micropost field 322 in amplification device 300. Actuation mechanism 340 is used to generate an actuation force in proximity to micropost field 320 that compels at least some of microposts 326 to exhibit motion. The actuation force may be, for example, a magnetic force. In one example, actuation mechanism 340 is a magnetic drive system consisting of a shaft mounted permanent magnet driven with a small brushless motor. The actuation rate can be, for example, from about less than 1k RPM to about 20k RPM.

Actuation mechanism 340 can be nested in a high-resolution heat block 345 (e.g., stability ±0.1° C.) to provide temperature control from about 25° C. to about 65° C. for isothermal nucleic acid amplification. By actuating microposts 326 and causing motion thereof, a sample fluid (not shown) in gap 314 is in effect stirred, mixed, or caused to flow or circulate within gap 314 of reaction chamber 316.

Hybrid Solid-Phase Amplification Assay

In one aspect, an amplification assay for detecting target nucleic acids in a sample fluid is a hybrid amplification assay, wherein a reaction solution or a portion of a reaction solution is set-up in a microtube on-bench and then loaded into a reaction chamber of a microfluidic amplification device.

Figure 5:
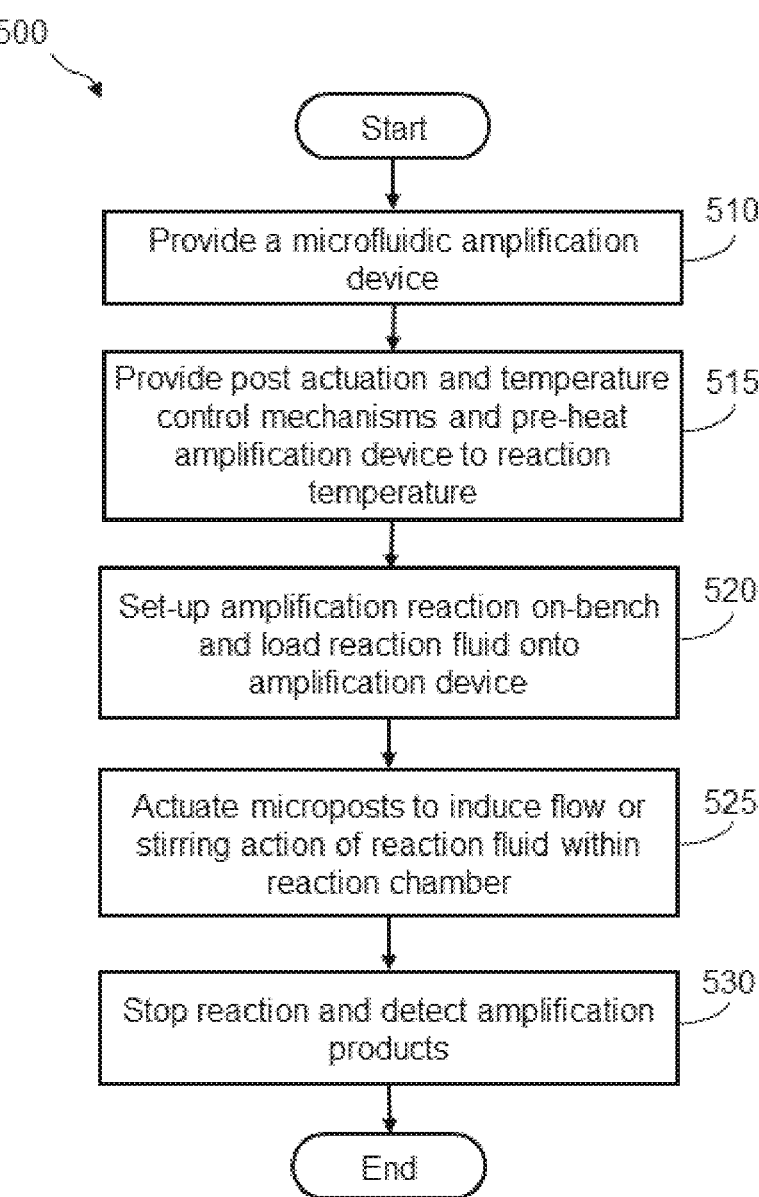
FIG. 5 is a flow diagram illustrating an example of a method of using a microfluidic amplification device for detecting nucleic acids in a sample using a hybrid bridge solid-phase amplification assay.

FIG. 5 is a flow diagram illustrating an example of a method 500 of using a microfluidic amplification device for detecting nucleic acids in a sample using a hybrid solid-phase amplification assay. In this example, primer spots on the hybridization surface include both forward and reverse primers for bridge amplification and the detection method uses the intercalating dye SYBR Green (Molecular Probes Inc.). Method 500 may include any or all the following steps as well as additional unspecified steps.

At a step 510, a microfluidic amplification device is provided. In one example, the amplification device is created by bonding a 50 μL "chamber" to a hybridization surface that includes an array of primer spots (i.e., forward, and reverse primers immobilized in close proximity) interspersed by microposts. The chamber walls are, for example, made from 220 μm double-sided adhesive, cut to the appropriate dimensions and bonded to 1 mm poly(methyl) methacrylate (PMMA) substrate to form the chamber ceiling. The PMMA substrate includes two (2) 1 mm through holes for fluid delivery and removal. In one example, the primer spots are forward and reverse primers that target Severe Acute Respiratory Syndrome Coronavirus 2 RNA virus (SARS-CoV-2; sequence information published by Behrmann, O., et al., Clinical Chemistry (2020) May 8: hvaa116).

At a step 515, mechanisms for post actuation and temperature control are provided. In one example, post actuation and temperature control are managed using the commercially available Redbud Lab's Stage device. The Stage device contains two (2) independent magnetic drive systems, allowing parallel processing of specimens, with each drive system consisting of a shaft mounted permanent magnet driven with a small brushless motor. Drive systems are nested in a high-resolution heat block (e.g., stability±0.1° C.) to provide temperature control from about 25° C. to about 65° C. for isothermal nucleic acid amplification. The amplification device is placed on the Stage device and pre-heated to a reaction temperature of about 38° C.

At a step 520, the amplification reaction is set-up in a microtube on-bench and loaded onto the amplification device. For example, a 50 μL RT-RPA reaction mixture that includes two (2) U reverse transcriptase (RT), twenty (20) U RNAase inhibitor, and 1× rehydration buffer is added to a freeze-dried RPA reaction pellet (TwistAmp Basic, TwistDx) on-bench in a microtube. An aliquot of sample is then added to the reaction tube. In one example, the sample is a synthetic SARS-CoV-2 RNA that is added to the reaction mixture at a concentration of ten (10) copies/μL. The reaction is initiated by the addition of 5 μL of 140 mM magnesium acetate and the contents of the microtube are loaded onto the amplification device pre-heated to 38° C. on the heat block of the Stage device.

At a step 525, the microposts are actuated to induce flow or stirring action of the reaction fluid within the chamber of the amplification device. In one example, a post drive frequency of about 10k RPM is used to actuate the microposts. Because of the flow created by the microposts, the target analytes are rapidly dispersed in the reaction fluid and bind to corresponding capture locations of the primer array. In one example, the microposts are actuated and the reaction is incubated for about ten (10) minutes. In another example, the microposts are actuated and the reaction is incubated for about twenty (20) minutes, an incubation period that is considered the typical upper limit for a typical point-of-care amplification assay.

At a step 530, the reaction is stopped, and the amplification products are detected. For example, at the end of the incubation period the reaction fluid is removed from the chamber using a 3× chamber volume flush of 0.1×SSC followed by a 3× volume flush of PBS. Hybridized amplicons at primer sites on the hybridization surface are stained using the intercalating dye SYBR Green (Molecular Probes Inc.). The hybridization surface (primer array) is then scanned using an Olympus IX83 inverted microscope with a motorized translation stage and the data is analyzed to determine the average spot intensity and standard deviation in intensities.

Method 500 of FIG. 5 can be modified for a solid-phase assay wherein only target-specific forward primers are immobilized on the hybridization surface of an amplification device and other assay components (e.g., corresponding reverse primer, sample, and assay reagents) are combined on-bench in a reaction solution and then loaded into the reaction chamber of the device. The amplification reactions with reverse primers in solution-phase are detected, for example, using a 5'-Cy5'-fluorescence modification to the reverse primer.

Evaluating System Performance

The performance of a microfluidic amplification device can be evaluated using a single target amplification assay with set experimental parameters and method 500 of FIG. 5 or a modification thereof. In one example, set experimental parameters include a single target nucleic acid concentration of ten (10) copies/µL, a post drive frequency of 10k RPM, and a ten (10)-minute incubation time. The performance of a microfluidic amplification device can be compared to a solid phase RT-RPA assay performed with static fluid (i.e., diffusion only, no micropost actuation) and/or reciprocal pumping.

In one aspect, the effect of post array/geometry (e.g., post density, lattice design, cross-sectional shape) on system performance can be evaluated in an amplification assay. At the end of the amplification assay, the hybridization surface (primer array) is then scanned for fluorescent detection and the data is analyzed to determine the average spot intensity and standard deviation in intensities.

In one aspect, a microfluidic amplification device can be further evaluated by testing the effect of drive frequency and chamber height (surface to volume ratio) on system performance. For example, drive frequency can be varied to provide an actuation rate ranging from 0 to 10k RPM, stepping in 2.5k increments. The surface to volume ratio (chamber height) can be from about 1 $\mu m^2/\mu L$ or from about 3 $\mu m^2/\mu L$ (standard) or from about 6 $\mu m^2/\mu L$.

The limit of detection (LOD) for a microfluidic amplification device can be determined using a single target assay with set experimental parameters and method 500 of FIG. 5 or a modification thereof. In one example, an LOD can be determined using a single nucleic acid target range from about $10^0$ copies/reaction chamber to about $10^5$ copies/reaction chamber and an incubation time of about twenty (20) minutes. The performance of a microfluidic amplification device can be compared to a solid phase RT-RPA assay performed with static fluid (i.e., diffusion only, no micropost actuation) and/or reciprocal pumping. The reciprocal pumping parameters can be selected to mimic those previously applied in published RPA assays (Kersting, S., et al., Mikrochim Acta (2014) 181 (13-14): 1715-1723, which is incorporated herein by reference in its entirety).

In one aspect, the LOD is determined for an amplification device with forward primers only immobilized on the hybridization surface (reverse primers included in the reaction solution) of the device.

In one aspect, the LOD is determined for an amplification device with forward and reverse primers immobilized on the hybridization surface of the device.

The LOD for a microfluidic amplification device can be determined using a multi-target assay with set experimental parameters and method 500 of FIG. 5 or a modification thereof. The multi-target assay can be used to represent a coinfection in a sample. For example, nucleic acid targets for the viral pathogens SARS-CoV-2 and respiratory syncytial virus (RSV) can be spiked into samples at ratios of 4:1, 1:1, and 1:4 and the LOD for the amplification device determined. The performance of a microfluidic amplification device can be compared to a solid phase RT-RPA assay performed with static fluid (i.e., diffusion only, no micropost actuation) and/or reciprocal pumping.

The effect of incubation time on the performance of a microfluidic amplification device can be determined using, for example, a single target assay with set experimental parameters and method 500 of FIG. 5 or a modification thereof. For example, a single target concentration of 10×LOD and incubation times of one (1), five (5), ten (10), fifteen (15), twenty (20), thirty (30), and sixty (60) minutes. The performance of a microfluidic amplification device can be compared to a solid phase RT-RPA assay performed with static fluid (i.e., diffusion only, no micropost actuation) and/or reciprocal pumping.

Multiplexed Point-of-Care Diagnostic Assay

The invention is useful for multiplexed testing for a panel of infectious pathogens in a single diagnostic nucleic acid amplification assay at a point-of-care (POC) setting. In one aspect, a POC microfluidic amplification device provides a "master mix" of reagents for a solid-phase RPA assay dried on an inner reaction chamber surface, wherein the dried reagent master mix is readily rehydrated by the addition of a sample fluid.

The number of intended targets (i.e., "plex") represented on the diagnostic array can be varied. In one aspect, a 125-plex array with 10 primer spots per disease is formed in a 5×10 array with a spot density of about twenty-five (25) target spots per $mm^2$ (i.e., 1,250 spots in the array).

In one aspect, a POC diagnostic assay is used to test for five (5) respiratory viral pathogens, SARS-CoV-2, Influenza, respiratory syncytial virus (RSV), and/or MERS-CoV, that may be present in a sample. Single-plex solution-phase RPA assays and primer sequences for SARS-CoV-2, Influenza, respiratory syncytial virus (RSV), and/or MERS-CoV have been published (Behrmann, O., et al., Clinical Chemistry (2020) May 8: hvaa116; Sun, N., et al., Analytical and Bioanalytical Chemistry (2019) 411(16): 3591-3602; Xu, Y.-z, et al., Molecular and Cellular Probes (2020) 49:101473; and Abd El Wahed, A., et al., PLoS Curr (2013) 5, which are incorporated herein by reference in its entirety). In the published assays, the limit of detection (LOD) for detection of viral RNA was five (5) to five hundred (500) copies/reaction.

Table 1 shows the primer design and sequence for the detection of SARS-CoV-2, Influenza A, Influenza B, RSV, and MERS-CoV (M=matrix gene; NS=non-structural protein; N=nucleocapsid).

TABLE 1

Respiratory virus panel, primer design, and sequence.

| Target | Gene | Primer | Primer squence (5' to 3') | Reference |
|---|---|---|---|---|
| Influenza A | M | MF146 | GGCTCTCATGGAATGGC TAAAGACAAGAC | Sun 2019 |
| | | MR425 | TTGTATATGAGGCCCAT GCAACTGGCAAGTG | |
| Influenza B | NS | B-F | TCTGCTGGAATTGAAGG GTTTGAGCCATAC | Sun 2012 |
| | | B-R | TCAAACGGAACTTCCCT TCTTTCTGAGTGT | |
| RSV | | RSV-F | TCCYARTTGTATAGCAT TCATAGGTGAAGGAG | Xu 2020 |
| | | RSV-R | TTGCATCTGTAGCAGGA ATGGTYAAATTYTCA | |
| SARS-CoV-2 | N | RPA-SARS-2-FW | CCTCTTCTCGTTCCTCA TCACGTAGTCGCAAC | Behrmann 2020 |
| | | RPA-SARS-2-RV | AGTGACAGTTTGGCCTT GTTGTTGTTGGCCTT | |

TABLE 1-continued

| Respiratory virus panel, primer design, and sequence. | | | | |
|---|---|---|---|---|
| Target | Gene | Primer | Primer squence (5' to 3') | Refer- ence |
| MERS- CoV | N | COR12 RT-RPA FP | AACTTCCACATTGAGGG GACTGGAGGCAA | Wahed 2013 |
| | | COR12 RT-RPA RP | AGAGTTTCCTGATCTTG AACCTTGTGAACT | |

Figure 6:
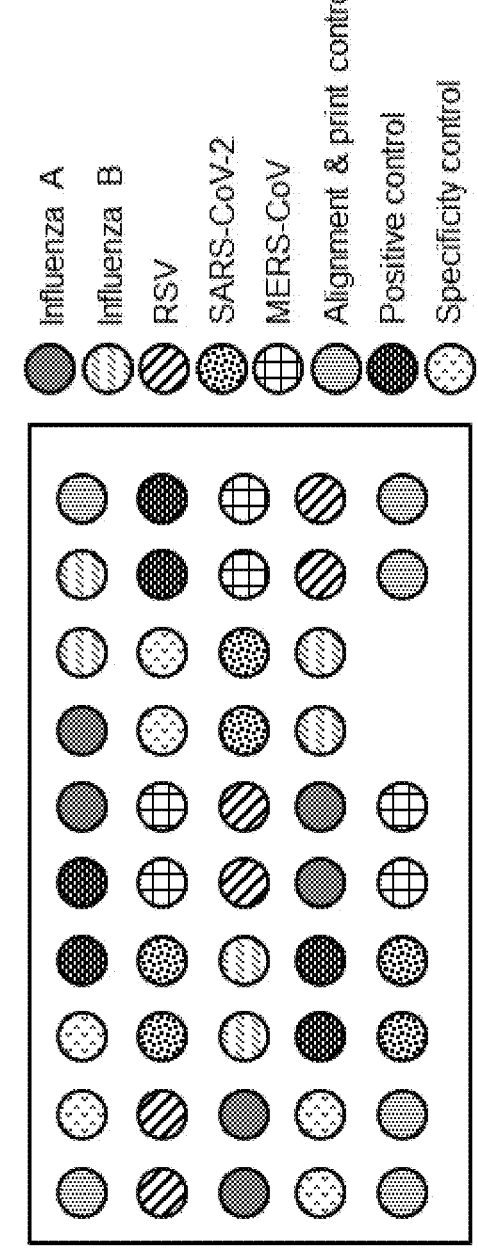
FIG. 6 is a schematic diagram illustrating an example of a layout of a primer array for detecting five (5) viral respiratory pathogens (SARS-CoV-2, Influenza A, Influenza B, RSV, and MERS-CoV).

FIG. 6 is a schematic diagram 600 illustrating an example of a layout of a primer array for detecting five (5) viral respiratory pathogens (SARS-CoV-2, Influenza A, Influenza B, RSV, and MERS-CoV). The hybridization surface of the amplification device is printed with both forward and reverse primers in each primer spot. In addition to the five (5) viral targets, a positive control (i.e., primers with sequence homology only to a synthetic sequence), a specificity control (i.e., an oligonucleotide with no sequence homology), and a combinational print fiducial (oligonucleotide with 5'-Cy5 modification) are included in the array. Each spot is replicated six (6) times for a total of forty-eight (48) spots on the array.

FIG. 7 is a flow diagram illustrating an example of a method 700 of testing for a panel of infectious pathogens in a single solid-phase nucleic acid amplification assay. Method 700 may include any or all the following steps as well as additional unspecified steps.

At a step 710, a microfluidic amplification device for solid-phase isothermal nucleic acid amplification is provided. In one example, the amplification device includes a primer array for five (5) RNA viruses plus three (3) process controls (e.g., an alignment and print control; a positive control; and a specificity control), and a dried (lyophilized) spot reagent of a master mix of RT-RPA assay reagents (e.g., enzymes, buffer, dNTPs, magnesium acetate). An example of the layout of the primer array for detecting the five (5) respiratory viruses is described in more detail with reference to FIG. 6 above.

At a step 715, mechanisms for post actuation and temperature control are provided. In one example, post actuation and temperature control are managed using the commercially available Redbud Lab's Stage device. The amplification device is placed on the Stage device and pre-heated to a reaction temperature of about 38° C.

At a step 720, a sample fluid is loaded into the reaction chamber of the amplification device.

At a step 725, the microposts are actuated to induce flow or stirring action of the sample fluid within the chamber of the amplification device. In one example, a post drive frequency of about 10k RPM is used to actuate the microposts. Because of the flow created by the microposts, the dried/lyophilized reagents are readily resuspended and homogenized in the sample fluid, and the target analytes are rapidly dispersed in the sample fluid and bind to their corresponding capture locations of the primer array. In one example, the microposts are actuated and the reaction is incubated for about twenty (20) minutes, an incubation period that is considered to be the upper limit for a typical point-of-care amplification assay.

At a step 730, the reaction is stopped, and the amplification products are detected. For example, the amplification reaction can be stopped by (i) removing the sample fluid from the reaction chamber of the microfluidic device after an incubation period and (ii) washing the capture probe array to remove non-hybridized reaction components. As a specific example, at the end of the incubation period, the reaction fluid is removed from the chamber using a 3× chamber volume flush of 0.1×SSC followed by a 3× volume flush of PBS.

Detection of an amplification product can be accomplished by either (i) a detection solution comprising a nucleic acid dye that is introduced into the reaction chamber of the microfluidic device, wherein binding of the nucleic acid dye to amplification products bound at a capture spot produces a detection signal or (ii) a fluorescence modification of a reverse primer provided in the sample fluid is used to provide a detection signal. For example, hybridized amplicons at primer sites on the hybridization surface are stained using the intercalating dye SYBR Green (Molecular Probes Inc.). The hybridization surface (primer array) is then scanned using, for example, an Olympus IX83 inverted microscope with a motorized translation stage and the data is analyzed to determine the average spot intensity and standard deviation in intensities. The intensity of off-target spots can be used to assess specificity. There are other methods or ways to measure the detection signal. For example, scanning the capture array for a (fluorescent) detection signal, then determining the fluorescence at an excitation/emission wavelength selected based on the nucleic acid dye or reverse primer fluorescent modification, and (c) then producing a measurement for assessing the presence of a target nucleic, wherein the measurement comprises calculating an average capture spot signal intensity and standard deviation in intensities.

At a step 735, positive and negative results are determined.

EXAMPLES

Microposts

FIG. 8 is a panel 800 of scanning electron microscope images showing soft magnetically actuatable microposts created using different templates. Microposts were formed of PDMS. Scale bars in each image (a) through (d) are 30 μm. Note that the bending in (a) and (d) is an artifact of preparation for imagining and is not intrinsic to the structure of the posts. Image (b) depicts circular cross section posts and images (a), (c), and (d) depict rectangular cross section posts. Image (c) is an overhead view of a "herringbone" rectangular cross section post array. The herringbone array was designed to create a phase lag between each post and its orthogonal nearest neighbor in a time varying magnetic field. A phase lag in beating between adjacent posts can create more efficient pumping and mixing in low Reynolds number environments (Lauga, E., Soft Matter (2011) 7(7): 3060-3065; Lauga, E., and D. Bartolo, Physical Review E (2008) 78(3): 030901; and Takagi, D., Phys Rev E Stat Nonlin Soft Matter Phys. (2015) 92(2): 023020, which are incorporated herein by reference in its entirety).

Figure 9:
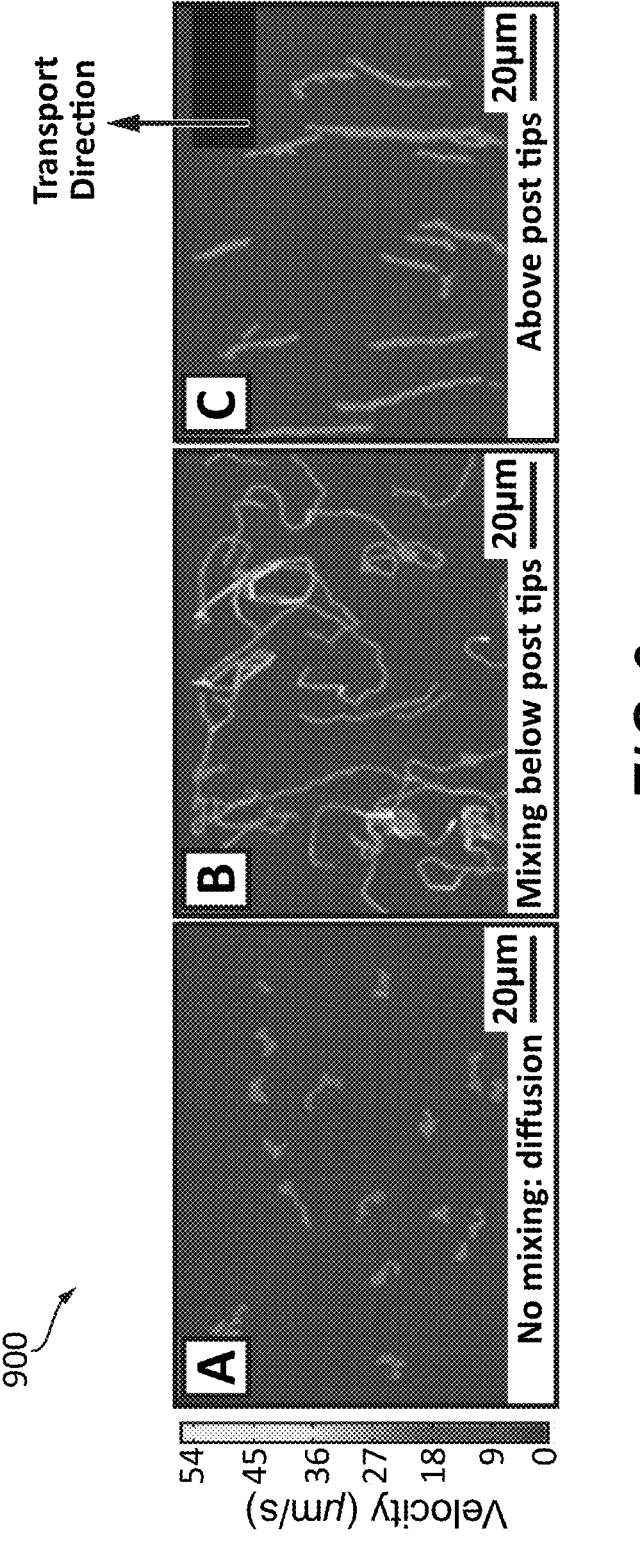
FIG. 9 is a panel of images showing the trajectories of 500-nm tracer beads in solution without and with micropost driven mixing.

FIG. 9 is a panel 900 of images showing the trajectories of 500-nm tracer beads in solution without and with micropost driven mixing. Velocities are averaged over a 0.25-s time window. Referring now to Panel (A), in the absence of micropost-driven mixing, the movement of the tracer beads is by diffusion. Referring now to Panel (B), in the presence of micropost-driven mixing, the movement of tracer beads below the tips (z=15 μm) of the micropost is non-directional, heterogeneous, and rapid, i.e., chaotic advection in the inter-post region. Referring now to Panel (C), in the presence of micropost-driven mixing, the movement of tracer beads above the tips (z=30 μm) of the microposts is unidirectional transport. Actuated, surface-attached microposts can simultaneously generate chaotic advection and directed flow (Shields, A. R., et al., Proceedings of the National Academy of Sciences (2010) 107(36): 15670-15675, which is incorporated herein by reference in its entirety). By contrast, other microfluidic mixing approaches such as herringbone mixers only increase the contact area for diffusion, but they do not increase the diffusion rate itself.

Actuatable microposts can accelerate reaction kinetics in microfluidic chambers by generating "microfluidic agitation". It is such "agitation" or movement that causes or results in the "flowing," "mixing," or "stirring" of fluids in microfluidic (reaction) chambers.

Figure 10:
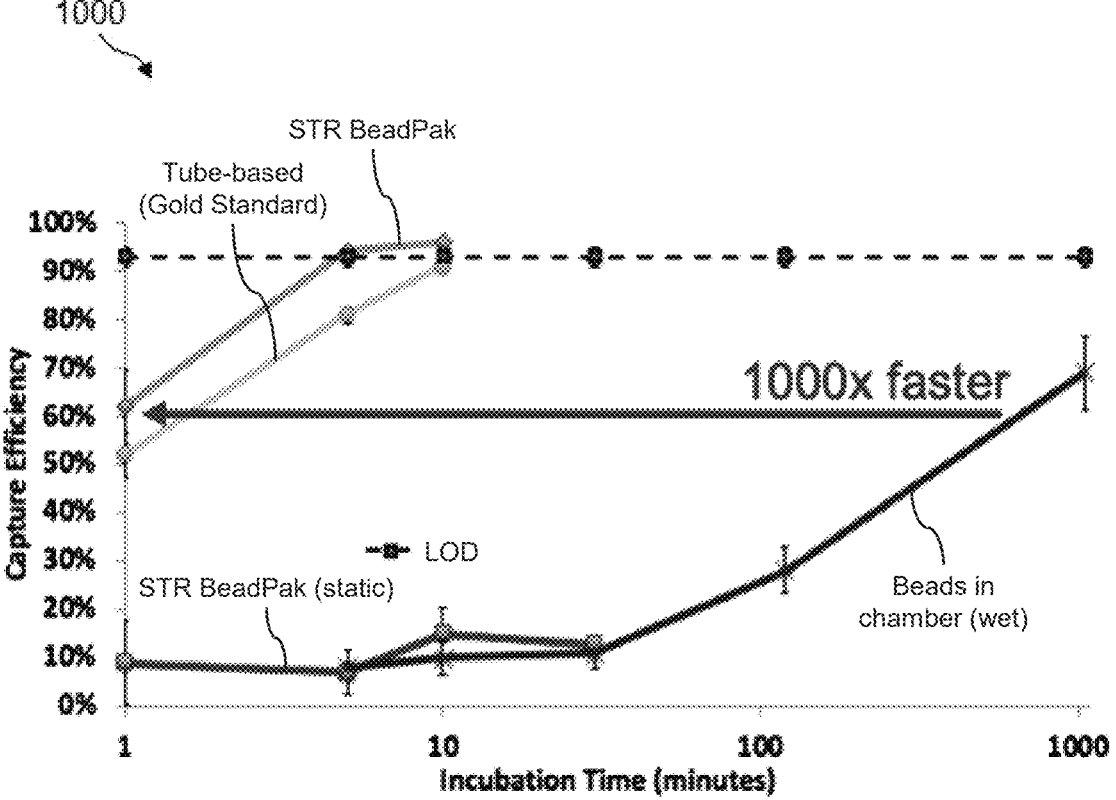
FIG. 10 is a plot showing the effect of microfluidic agitation on bead capture kinetics in a microfluidic chamber.

FIG. 10 is a plot 1000 showing the effect of microfluidic agitation on bead capture kinetics in a microfluidic chamber. In this experiment, magnetically responsive capture beads were placed in a microfluidic chamber that included an array of microposts on the chamber floor ("STR BeadPak"); a "typical" chamber; and in a micro-tube. A target sample was introduced into the reaction chambers and micro-tube, and the efficiency of target capture on the capture beads was determined. The data show that actuation of microposts (i.e., "STR BeadPak" line) to create a stirring/mixing action in the sample solution improved magnetic bead capture performance in a microfluidic environment up to about 1,000× faster than static chambers, i.e., "STR BeadPak (static) line" and "Beads in chamber (wet) line." The data also shows that actuation of microposts in a microfluidic environment restores capture efficiency to levels equal to or greater than the "gold standard" micro-tube-based assays run on a rocker platform according to the manufacturer's recommended protocol (i.e., "Tube-based (Gold Standard)" line).

FIG. 11 is a pair of screenshots 1100 of an example of rehydrating a dried reagent spot in a microfluidic amplification device. In this example, a PCR master mix solution that included a (blue) dye was lyophilized on the chamber substrate surface opposing the hybridization surface (i.e., the micropost/primer array substrate). Panel A shows the dried reagent spot localized in the reaction chamber. A sample fluid was loaded into the reaction chamber of the device and the microposts were actuated for three (3) minutes. Panel B shows the dispersed throughout the chamber after rehydration with the sample fluid and mixing by the microposts.

Array Printing

To demonstrate the feasibility of using a soft lithography process to print an array, a PDMS stamp was used to pattern IgG antibodies onto a glass substrate and a soft polyacrylamide substrate.

Figure 12:
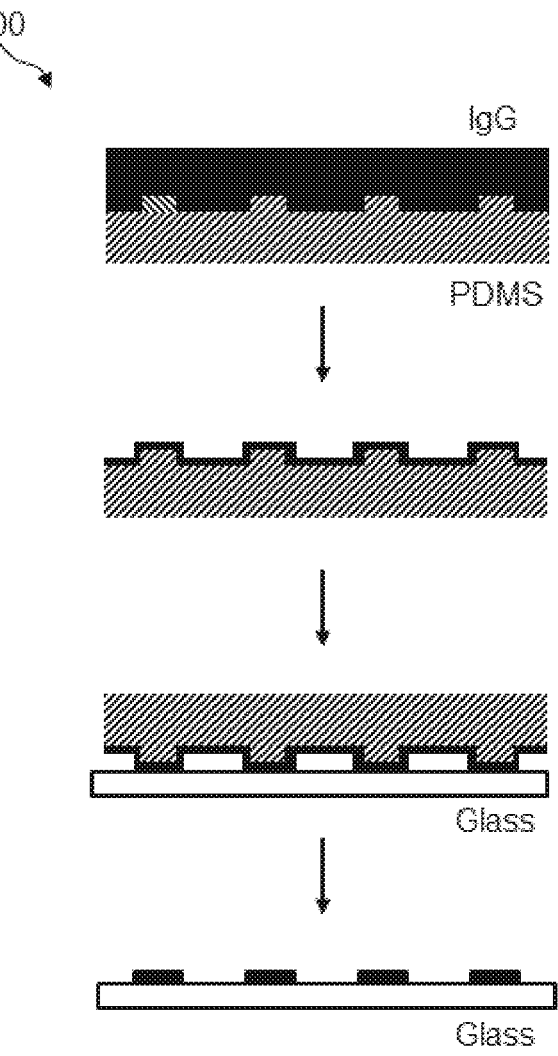
FIG. 12 is a schematic diagram showing a soft lithography process for creating a stamp for printing an array on a micropost substrate surface.

FIG. 12 is a schematic diagram 1200 showing a soft lithography process for creating a stamp for printing an array on a micropost substrate surface. The pattern-filled structure represents a PDMS stamp that has been molded on a silicon or SU-8 master fabricated using standard photolithography. The black top layer "IgG" denotes an antibody film that is used to coat the PDMS stamp. The coated PDMS stamp is used to pattern IgG proteins onto a glass substrate.

Figure 13A:
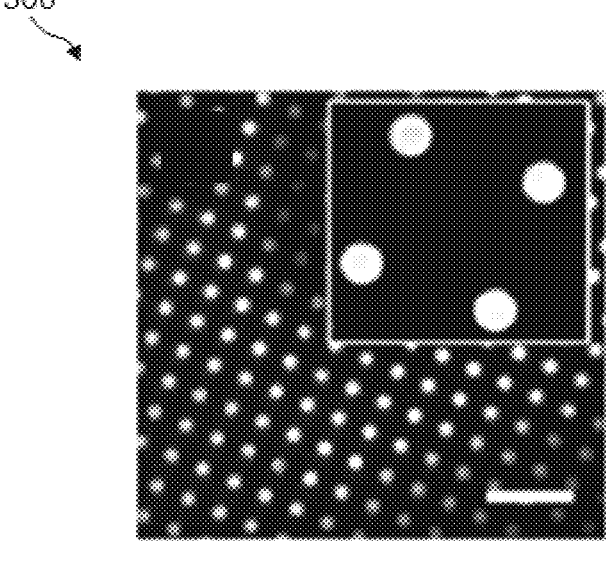
FIG. 13A is a photograph showing the actual stamped IgG pattern on a glass substrate.

FIG. 13A is a photograph 1300 showing the actual stamped IgG pattern on a glass substrate. Scale bar=20 μm. The inset in FIG. 13A shows 2 μm IgG spots at 8 μm spacing.

Figure 13B:
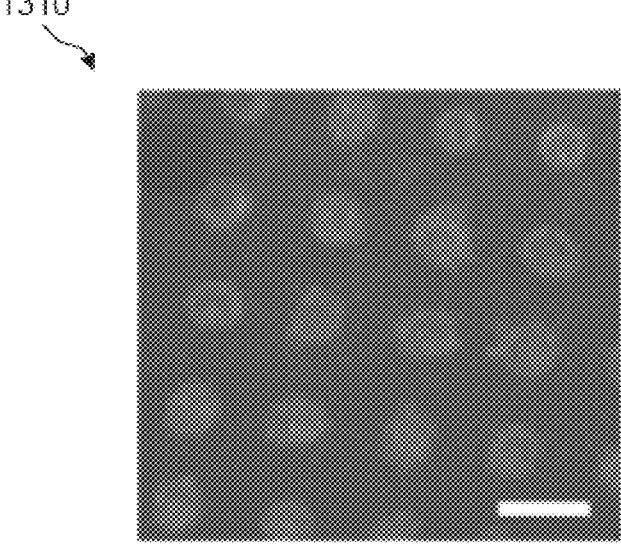
FIG. 13B is a photograph showing IgG stamped onto a soft polyacrylamide substrate (55 kPa).

FIG. 13B is a photograph 1310 showing IgG stamped onto a soft polyacrylamide substrate (55 kPa). Scale bar=20 μm.

Although the foregoing subject matter has been described in some detail by way of illustration and example for purposes of clarity of understanding, it will be understood by those skilled in the art that certain changes and modifications can be practiced within the scope of the appended claims.

We claim:

1. A microfluidic device for nucleic acid amplification, wherein the microfluidic device comprises:
   a) a reaction chamber formed between at least two substrates, wherein the reaction chamber further comprises:
      i) a micropost field formed on one or more surfaces of the reaction chamber and comprising a plurality of surface-attached actuatable microposts arranged thereon;
      ii) a capture probe array wherein the capture probe array comprises a plurality of capture spots patterned on a reaction surface among the micropost field; and
      iii) at least one fluid inlet port and at least one fluid outlet port arranged for flowing one or more liquids into and/or out of the reaction chamber.

2. The microfluidic device of claim 1, wherein the reaction chamber has a volume ranging from about 1 μm²/μL to about 100 μm²/μL, from about 1 μm²/μL to about 50 μm²/μL, from about 1 μm²/μL to about 25 μm²/μL, or from about 1 μm²/μL to about 10 μm²/μL.

3. The microfluidic device of claim 1, wherein the micropost field is provided on an inner surface of the bottom substrate of the reaction chamber.

4. The microfluidic device of claim 1, wherein the plurality of surface-attached microposts in the micropost field are arranged to provide regularly spaced post-free regions.

5. The microfluidic device of claim 1, wherein the microposts are layered onto the surface of the chamber using a backing substrate, and wherein the microposts and the backing substrate comprise a magnetoelastomeric material.

6. The microfluidic device of claim 1, wherein the surface-attached microposts in the reaction chamber are configured for actuation in the presence of an actuation force.

7. The microfluidic device of claim 1, wherein one or more of the capture spots comprises a plurality of immobilized oligonucleotide primers for capture and/or amplification of a target-specific nucleic acid in the sample fluid.

8. The microfluidic device of claim 7, wherein the immobilized oligonucleotide primers comprise a mixture of forward and reverse primers.

9. The microfluidic device of claim 8, wherein the mixture of forward and reverse primers is immobilized on a capture spot in proximity sufficient to enable bridge amplification detection of a nucleic acid target.

10. The microfluidic device of claim 1, wherein the capture spots are positioned within a defined arrangement of surface-attached microposts on a reaction surface.

11. The microfluidic device of claim 1, wherein the at least one fluid inlet port and the at least one fluid outlet port are provided in the top substrate of the microfluidic device.

12. The microfluidic device of claim 1, further comprising a dried reagent spot on an inner surface, wherein:
   a) the dried reagent spot comprises one or more reagent components for performing a nucleic acid amplification assay; and
   b) the dried reagent spot is selected to be capable of rehydration by a sample fluid in the reaction chamber.

13. The microfluidic device of claim 12, wherein the dried reagent spot is provided on the inner surface of the top substrate of the reaction chamber of the microfluidic device.

14. The microfluidic device of claim 12, wherein the dried reagent spot comprises one or more reagent components for performing an isothermal amplification reaction.

15. The microfluidic device of claim 14, wherein the isothermal amplification reaction comprises at least one of a loop-mediated isothermal amplification (LAMP) assay, a recombinase polymerase amplification (RPA) assay, or a reverse transcription recombinase polymerase amplification (RT-RPA) assay.

16. The microfluidic device of claim 12, wherein the dried reagent spot comprises one or more reagent components of a non-isothermal amplification reaction.

17. The microfluidic device of claim 16, wherein the non-isothermal amplification reaction comprises a polymerase chain reaction assay (PCR).

18. A system for nucleic acid amplification, wherein the system comprises:
   a) the microfluidic device of claim 1;
   b) an actuation mechanism for applying an actuation force to the reaction chamber of the microfluidic device to actuate movement of at least some of the surface-attached microposts;
   c) a temperature control mechanism for maintaining a reaction temperature; and d) a detection mechanism for detecting amplification products.

19. The system of claim 18, wherein the actuation force is chosen from a group consisting of a magnetic force, a thermal force, a sonic force, or an electric force.

20. The system of claim 19, wherein the actuation force is applied as a function of frequency or amplitude or as an impulse force.

21. The system of claim 18, wherein the actuation mechanism comprises a magnetic drive system.

22. The system of claim 21, wherein the magnetic drive system comprises a shaft mounted permanent magnet that is driven by a small brushless motor.

23. The system of claim 21, wherein the magnetic drive system is configured for providing an actuation rate of from about less than 1K RPM to about 20K RPM.

24. The system of claim 18, wherein the temperature control mechanism comprises a high-resolution heat block that is configured to provide temperature control from about 25° C. to about 95° C.

25. The system of claim 18, wherein the nucleic acid amplification system further comprises a housing configured for removably receiving the microfluidic device.

* * * * *